US011426291B2

(12) United States Patent
Nebosky et al.

(10) Patent No.: US 11,426,291 B2
(45) Date of Patent: Aug. 30, 2022

(54) ORTHOPAEDIC IMPLANT WITH POROUS STRUCTURAL MEMBER

(71) Applicant: SMed-TA/TD, LLC, Columbia City, IN (US)

(72) Inventors: Paul S. Nebosky, Fort Wayne, IN (US); Gregory C. Stalcup, Fort Wayne, IN (US); Troy D. Knapp, Hammond, WI (US)

(73) Assignee: SMed-TA/TD, LLC, Columbia City, IN (US)

( * ) Notice: Subject to any disclaimer, the term of this patent is extended or adjusted under 35 U.S.C. 154(b) by 44 days.

(21) Appl. No.: 17/076,369

(22) Filed: Oct. 21, 2020

(65) Prior Publication Data

US 2021/0030559 A1 Feb. 4, 2021

Related U.S. Application Data

(60) Division of application No. 15/878,723, filed on Jan. 24, 2018, now Pat. No. 10,842,645, which is a
(Continued)

(51) Int. Cl.
*A61F 2/44* (2006.01)
*A61F 2/46* (2006.01)
*A61F 2/30* (2006.01)

(52) U.S. Cl.
CPC ............... *A61F 2/447* (2013.01); *A61F 2/30* (2013.01); *A61F 2/3094* (2013.01);
(Continued)

(58) Field of Classification Search
None
See application file for complete search history.

(56) References Cited

U.S. PATENT DOCUMENTS 3,662,405 A 5/1972 Bortz et al.
3,683,421 A 8/1972 Martinie
(Continued)

FOREIGN PATENT DOCUMENTS

DE 4211345 C1 11/1993
DE 4423020 A1 1/1996
(Continued)

OTHER PUBLICATIONS

Office Action dated Jan. 5, 2010 in U.S. Appl. No. 11/060,377 (10 pages).
(Continued)

*Primary Examiner* — Tessa M Matthews
(74) *Attorney, Agent, or Firm* — Taylor IP, P.C.

(57) ABSTRACT

A tool for use with an orthopaedic implant includes: a tubular assembly including a tubular passage having a first end and a second end, the first end including a means for attachment to an implant body; a plug; and a plunger coupled to the plug. The tubular passage is configured to receive, via the second end, a material agent and the plunger coupled to the plug. The plunger is configured to slide through the tubular passage for expelling the material agent from the tubular passage into a load bearing member via the at least one first opening. The plunger is configured to rotate within the tubular passage for coupling the plug with the first opening to seal the first opening against expulsion of the material agent from the load bearing member via the first opening.

8 Claims, 17 Drawing Sheets

Related U.S. Application Data continuation-in-part of application No. 15/626,596, filed on Jun. 19, 2017, which is a division of application No. 14/637,142, filed on Mar. 3, 2015, now Pat. No. 9,700,431, which is a continuation-in-part of application No. 12/540,515, filed on Aug. 13, 2009, now abandoned.

(60) Provisional application No. 61/088,460, filed on Aug. 13, 2008.

(52) U.S. Cl.
CPC .......... *A61F 2/4455* (2013.01); *A61F 2/4465* (2013.01); *A61F 2/4611* (2013.01); *A61F 2/30965* (2013.01); *A61F 2002/305* (2013.01); *A61F 2002/3008* (2013.01); *A61F 2002/30011* (2013.01); *A61F 2002/30028* (2013.01); *A61F 2002/3092* (2013.01); *A61F 2002/3093* (2013.01); *A61F 2002/3097* (2013.01); *A61F 2002/30261* (2013.01); *A61F 2002/30322* (2013.01); *A61F 2002/30387* (2013.01); *A61F 2002/30451* (2013.01); *A61F 2002/30492* (2013.01); *A61F 2002/30593* (2013.01); *A61F 2002/30599* (2013.01); *A61F 2002/30622* (2013.01); *A61F 2002/30677* (2013.01); *A61F 2002/30733* (2013.01); *A61F 2002/30841* (2013.01); *A61F 2002/30967* (2013.01); *A61F 2002/30971* (2013.01); *A61F 2002/4629* (2013.01); *A61F 2310/00017* (2013.01); *A61F 2310/00023* (2013.01); *A61F 2310/00203* (2013.01); *A61F 2310/00293* (2013.01)

(56) References Cited

U.S. PATENT DOCUMENTS

| | | |
|---|---|---|
| 3,855,638 A | 12/1974 | Pilliar |
| 3,867,728 A | 2/1975 | Stubstad et al. |
| 4,011,602 A | 3/1977 | Rybicki et al. |
| 4,060,081 A | 11/1977 | Yannas et al. |
| 4,156,943 A | 6/1979 | Collier |
| 4,222,128 A | 9/1980 | Tomonaga et al. |
| 4,450,150 A | 5/1984 | Sidman |
| 4,453,537 A | 6/1984 | Spitzer |
| 4,485,097 A | 11/1984 | Bell |
| 4,520,821 A | 6/1985 | Schmidt et al. |
| 4,608,052 A | 8/1986 | Van Kampen et al. |
| 4,609,551 A | 9/1986 | Caplan et al. |
| 4,620,327 A | 11/1986 | Caplan et al. |
| 4,644,627 A | 2/1987 | Palazzo |
| 4,660,755 A | 4/1987 | Farling et al. |
| 4,737,411 A | 4/1988 | Graves, Jr. et al. |
| 4,769,041 A | 9/1988 | Morscher |
| 4,833,271 A * | 5/1989 | Nelson .................. C07C 405/00 562/503 |
| 4,846,834 A | 7/1989 | Von Recum et al. |
| 4,858,603 A | 8/1989 | Clemow et al. |
| 4,936,859 A | 6/1990 | Morscher et al. |
| 4,976,738 A | 12/1990 | Frey et al. |
| 5,030,233 A | 7/1991 | Ducheyne |
| 5,041,107 A | 8/1991 | Heil, Jr. |
| 5,084,051 A | 1/1992 | Tormala et al. |
| 5,092,898 A | 3/1992 | Bekki et al. |
| 5,100,392 A | 3/1992 | Orth et al. |
| 5,104,410 A | 4/1992 | Chowdhary |
| 5,190,550 A | 3/1993 | Miller et al. |
| 5,197,985 A | 3/1993 | Caplan et al. |
| 5,204,055 A | 4/1993 | Sachs et al. |
| 5,219,363 A | 6/1993 | Crowninshield et al. |
| 5,226,914 A | 7/1993 | Caplan et al. |
| 5,281,210 A | 1/1994 | Burke et al. |
| 5,282,861 A | 2/1994 | Kaplan |
| 5,306,309 A | 4/1994 | Wagner et al. |
| 5,328,765 A | 7/1994 | Anderson et al. |
| 5,370,690 A | 12/1994 | Barrett |
| 5,380,328 A | 1/1995 | Morgan |
| 5,443,471 A | 8/1995 | Swajger |
| 5,458,643 A | 10/1995 | Oka et al. |
| 5,462,362 A | 10/1995 | Yuhta et al. |
| 5,490,962 A | 2/1996 | Cima et al. |
| 5,496,372 A | 3/1996 | Hamamoto et al. |
| 5,514,182 A | 5/1996 | Shea |
| 5,518,680 A | 5/1996 | Cima et al. |
| 5,531,750 A | 7/1996 | Even-Esh |
| 5,534,028 A | 7/1996 | Bao et al. |
| 5,537,851 A | 7/1996 | Sheu et al. |
| 5,549,700 A | 8/1996 | Graham et al. |
| 5,571,187 A | 11/1996 | Devanathan |
| 5,593,443 A | 1/1997 | Carter et al. |
| 5,637,175 A | 6/1997 | Feygin et al. |
| 5,641,323 A | 6/1997 | Caldarise |
| 5,702,449 A | 12/1997 | McKay |
| 5,730,817 A | 3/1998 | Feygin et al. |
| 5,732,469 A | 3/1998 | Hamamoto et al. |
| 5,750,103 A | 5/1998 | Cherksey |
| 5,769,897 A | 6/1998 | Harle |
| 5,776,199 A | 7/1998 | Michelson |
| 5,800,828 A | 9/1998 | Dionne et al. |
| 5,807,406 A | 9/1998 | Brauker et al. |
| 5,848,989 A | 12/1998 | Villani |
| 5,849,015 A | 12/1998 | Haywood et al. |
| 5,869,170 A | 2/1999 | Cima et al. |
| 5,871,484 A | 2/1999 | Spievack et al. |
| 5,876,550 A | 3/1999 | Feygin et al. |
| 5,879,406 A | 3/1999 | Lilley |
| 5,916,269 A | 6/1999 | Serbousek et al. |
| 5,971,985 A | 10/1999 | Carchidi et al. |
| 5,989,250 A | 11/1999 | Wagner et al. |
| 6,010,336 A | 1/2000 | Shimotoso et al. |
| 6,037,519 A | 3/2000 | McKay |
| 6,045,581 A | 4/2000 | Burkinshaw |
| 6,110,179 A | 8/2000 | Flivik et al. |
| 6,136,029 A | 10/2000 | Johnson et al. |
| 6,136,031 A | 10/2000 | Middleton |
| 6,139,574 A | 10/2000 | Vacanti et al. |
| 6,143,035 A | 11/2000 | McDowell |
| 6,159,247 A | 12/2000 | Klawitter et al. |
| 6,176,874 B1 | 1/2001 | Vacanti et al. |
| 6,200,347 B1 | 3/2001 | Anderson et al. |
| 6,238,435 B1 | 5/2001 | Meulink et al. |
| 6,283,997 B1 | 9/2001 | Garg et al. |
| 6,290,726 B1 | 9/2001 | Pope et al. |
| 6,306,424 B1 | 10/2001 | Vyakarnam et al. |
| 6,315,797 B1 | 11/2001 | Middleton |
| 6,322,564 B1 | 11/2001 | Surma |
| 6,328,765 B1 | 12/2001 | Hardwick et al. |
| 6,333,029 B1 | 12/2001 | Vyakarnam et al. |
| 6,337,198 B1 | 1/2002 | Levene et al. |
| 6,365,149 B2 | 4/2002 | Vyakarnam et al. |
| 6,379,385 B1 | 4/2002 | Kalas et al. |
| 6,379,391 B1 | 4/2002 | Masini |
| 6,395,011 B1 | 5/2002 | Johanson et al. |
| 6,409,764 B1 | 6/2002 | White et al. |
| 6,419,704 B1 | 7/2002 | Ferree |
| 6,423,095 B1 | 7/2002 | Van Hoeck et al. |
| 6,423,252 B1 | 7/2002 | Chun et al. |
| 6,425,921 B1 | 7/2002 | Grundei et al. |
| 6,440,734 B1 | 8/2002 | Pykett et al. |
| 6,454,811 B1 | 9/2002 | Sherwood et al. |
| 6,458,162 B1 | 10/2002 | Koblish et al. |
| 6,461,385 B1 | 10/2002 | Gayer et al. |
| 6,471,689 B1 | 10/2002 | Joseph et al. |
| 6,471,993 B1 | 10/2002 | Shastri et al. |
| 6,475,137 B1 | 11/2002 | Elist |
| 6,494,916 B1 | 12/2002 | Babalola et al. |
| 6,514,514 B1 | 2/2003 | Atkinson et al. |
| 6,520,993 B2 | 2/2003 | James et al. |
| 6,526,984 B1 | 3/2003 | Nilsson et al. |
| 6,527,810 B2 | 3/2003 | Johnson et al. |
| 6,530,958 B1 | 3/2003 | Cima et al. |
| 6,533,818 B1 | 3/2003 | Weber et al. |

(56) References Cited

U.S. PATENT DOCUMENTS

| | | |
|---|---|---|
| 6,534,084 B1 | 3/2003 | Vyakarnam et al. |
| 6,544,472 B1 | 4/2003 | Compton et al. |
| 6,547,824 B1 | 4/2003 | Price |
| 6,551,290 B1 | 4/2003 | Elsbery et al. |
| 6,554,857 B1 | 4/2003 | Zilla et al. |
| 6,565,572 B2 | 5/2003 | Chappius |
| 6,571,130 B1 | 5/2003 | Ljungstroem et al. |
| 6,599,322 B1 | 7/2003 | Amrich et al. |
| 6,610,095 B1 | 8/2003 | Pope et al. |
| 6,626,950 B2 | 9/2003 | Brown et al. |
| 6,635,049 B1 | 10/2003 | Robinson et al. |
| 6,638,310 B2 | 10/2003 | Lin et al. |
| 6,645,251 B2 | 11/2003 | Salehi et al. |
| 6,656,489 B1 | 12/2003 | Mahmood et al. |
| 6,660,040 B2 | 12/2003 | Chan et al. |
| 6,673,108 B2 | 1/2004 | Zilla et al. |
| 6,682,567 B1 | 1/2004 | Schroeder |
| 6,692,528 B2 | 2/2004 | Ward et al. |
| 6,709,463 B1 | 3/2004 | Pope et al. |
| 6,709,464 B2 | 3/2004 | Scott et al. |
| 6,712,850 B2 | 3/2004 | Vyakarnam et al. |
| 6,723,120 B2 | 4/2004 | Yan |
| 6,736,850 B2 | 5/2004 | Davis |
| 6,749,636 B2 | 6/2004 | Michelson |
| 6,758,863 B2 | 7/2004 | Estes et al. |
| 6,783,546 B2 | 8/2004 | Zucherman et al. |
| 6,818,620 B2 | 11/2004 | Bhatnagar |
| 6,852,272 B2 | 2/2005 | Artz et al. |
| 6,855,167 B2 | 2/2005 | Shimp et al. |
| 6,863,899 B2 | 3/2005 | Koblish et al. |
| 6,866,685 B2 | 3/2005 | Chan et al. |
| 6,881,413 B1 | 4/2005 | Bartholeyns |
| 6,893,465 B2 | 5/2005 | Huang |
| 6,913,623 B1 | 7/2005 | Zhu |
| 6,916,321 B2 | 7/2005 | TenHuisen et al. |
| 6,958,078 B2 | 10/2005 | Goel et al. |
| 6,969,383 B2 | 11/2005 | Hildebrand |
| 6,979,353 B2 | 12/2005 | Bresina |
| 6,989,033 B1 | 1/2006 | Schmidt |
| 6,993,406 B1 | 1/2006 | Cesarano, III et al. |
| 7,018,416 B2 | 3/2006 | Hanson et al. |
| 7,018,418 B2 | 3/2006 | Amrich et al. |
| 7,052,710 B2 | 5/2006 | Giordano et al. |
| 7,077,867 B1 | 7/2006 | Pope et al. |
| 7,087,086 B2 | 8/2006 | Li et al. |
| 7,087,200 B2 | 8/2006 | Taboas et al. |
| 7,090,668 B1 | 8/2006 | U et al. |
| 7,094,371 B2 | 8/2006 | Lo |
| 7,108,828 B2 | 9/2006 | Lefebvre et al. |
| 7,112,223 B2 | 9/2006 | Davis |
| 7,128,762 B2 | 10/2006 | Middleton |
| D533,277 S | 12/2006 | Blain |
| 7,174,282 B2 | 2/2007 | Hollister et al. |
| 7,189,409 B2 | 3/2007 | Pirhonen et al. |
| 7,192,440 B2 | 3/2007 | Andreas et al. |
| D539,934 S | 4/2007 | Blain |
| 7,208,222 B2 | 4/2007 | Rolfe et al. |
| D541,940 S | 5/2007 | Blain |
| 7,226,612 B2 | 6/2007 | Sohier et al. |
| 7,238,186 B2 | 7/2007 | Zdeblick et al. |
| 7,238,363 B2 | 7/2007 | Mansouri et al. |
| 7,250,055 B1 | 7/2007 | Vanderwalle |
| 7,250,060 B2 | 7/2007 | Trieu |
| 7,255,713 B2 | 8/2007 | Malek |
| 7,300,439 B2 | 11/2007 | May |
| D564,095 S | 3/2008 | Blain |
| D566,276 S | 4/2008 | Blain |
| 7,354,452 B2 | 4/2008 | Foley |
| 7,537,617 B2 | 5/2009 | Bindsell et al. |
| 7,537,664 B2 | 5/2009 | O'Neill et al. |
| D594,986 S | 6/2009 | Miles et al. |
| D599,019 S | 8/2009 | Pimenta et al. |
| 7,575,572 B2 | 8/2009 | Sweeney |
| 7,632,228 B2 | 12/2009 | Brauker et al. |
| 7,632,338 B2 | 12/2009 | Cipollini |
| 7,666,230 B2 | 2/2010 | Orban et al. |
| 7,674,426 B2 | 3/2010 | Grohowski, Jr. |
| 7,674,477 B1 | 3/2010 | Schmid et al. |
| D616,546 S | 5/2010 | Vraney et al. |
| 7,717,956 B2 | 5/2010 | Lang |
| D619,719 S | 7/2010 | Pannu |
| D620,114 S | 7/2010 | Henriquez |
| D620,115 S | 7/2010 | Pannu |
| D620,116 S | 7/2010 | Pannu |
| D621,509 S | 8/2010 | Lovell |
| D627,467 S | 11/2010 | Pannu |
| D627,468 S | 11/2010 | Richter et al. |
| 7,833,271 B2 | 11/2010 | Mitchell et al. |
| 7,875,080 B2 | 1/2011 | Puno et al. |
| 7,909,870 B2 | 3/2011 | Kraus |
| 7,910,124 B2 | 3/2011 | Boyan et al. |
| 7,963,995 B2 | 6/2011 | Richelsoph |
| 8,062,372 B2 | 11/2011 | Tsuang et al. |
| 8,066,750 B2 | 11/2011 | Oi et al. |
| 8,147,521 B1 | 4/2012 | Cornwall et al. |
| D671,645 S | 11/2012 | Curran et al. |
| D674,092 S | 1/2013 | Lovell |
| 8,496,706 B2 | 7/2013 | Ragab et al. |
| 8,568,482 B2 | 10/2013 | Kraus et al. |
| 8,623,088 B1 | 1/2014 | Tohmeh et al. |
| 8,685,099 B2 | 4/2014 | Bhattacharya et al. |
| D770,045 S | 10/2016 | Curran et al. |
| 2001/0038848 A1 | 11/2001 | Donda et al. |
| 2001/0039455 A1 | 11/2001 | Simon et al. |
| 2002/0022884 A1 | 2/2002 | Mansmann |
| 2002/0029083 A1 | 3/2002 | Zucherman et al. |
| 2002/0035400 A1 | 3/2002 | Bryan et al. |
| 2002/0062154 A1 | 5/2002 | Ayers |
| 2002/0072798 A1 | 6/2002 | Riesle et al. |
| 2002/0091447 A1 | 7/2002 | Shimp et al. |
| 2002/0106393 A1 | 8/2002 | Bianchi et al. |
| 2002/0128715 A1 | 9/2002 | Bryan et al. |
| 2002/0143402 A1 | 10/2002 | Steinberg |
| 2002/0147497 A1* | 10/2002 | Belef ............... A61F 2/442 623/908 |
| 2002/0161447 A1 | 10/2002 | Salehi et al. |
| 2002/0182241 A1 | 12/2002 | Borenstein et al. |
| 2002/0183850 A1 | 12/2002 | Felt et al. |
| 2002/0197178 A1 | 12/2002 | Yan |
| 2003/0003127 A1 | 1/2003 | Brown et al. |
| 2003/0004578 A1 | 1/2003 | Brown et al. |
| 2003/0006534 A1 | 1/2003 | Taboas et al. |
| 2003/0012805 A1 | 1/2003 | Chen et al. |
| 2003/0023311 A1 | 1/2003 | Trieu |
| 2003/0055506 A1 | 3/2003 | Stoy et al. |
| 2003/0060886 A1 | 3/2003 | Van Hoeck et al. |
| 2003/0060891 A1 | 3/2003 | Shah |
| 2003/0069465 A1 | 4/2003 | Benkowski et al. |
| 2003/0097182 A1 | 5/2003 | Buchman et al. |
| 2003/0105527 A1 | 6/2003 | Bresina |
| 2003/0114934 A1 | 6/2003 | Steinberg |
| 2003/0114936 A1 | 6/2003 | Sherwood et al. |
| 2003/0118649 A1 | 6/2003 | Gao et al. |
| 2003/0120344 A1 | 6/2003 | Michelson |
| 2003/0125739 A1 | 7/2003 | Bagga et al. |
| 2003/0130743 A1 | 7/2003 | Scott et al. |
| 2003/0139809 A1 | 7/2003 | Worst et al. |
| 2003/0171738 A1 | 9/2003 | Konieczynski et al. |
| 2003/0171820 A1 | 9/2003 | Wilshaw et al. |
| 2003/0180171 A1 | 9/2003 | Artz et al. |
| 2003/0187513 A1 | 10/2003 | Durniak |
| 2003/0203002 A1 | 10/2003 | Murphy et al. |
| 2003/0206928 A1 | 11/2003 | Tormala et al. |
| 2003/0208274 A1 | 11/2003 | Davis |
| 2004/0024470 A1 | 2/2004 | Giordano et al. |
| 2004/0034357 A1 | 2/2004 | Beane et al. |
| 2004/0034427 A1 | 2/2004 | Goel et al. |
| 2004/0063206 A1 | 4/2004 | Rowley et al. |
| 2004/0073197 A1 | 4/2004 | Kim |
| 2004/0115172 A1 | 6/2004 | Bianchi et al. |
| 2004/0126405 A1 | 7/2004 | Sahatjian et al. |
| 2004/0147905 A1 | 7/2004 | Krumme |
| 2004/0153165 A1 | 8/2004 | Li et al. |
| 2004/0180072 A1 | 9/2004 | Tunc et al. |

(56) References Cited

U.S. PATENT DOCUMENTS

| | | |
|---|---|---|
| 2004/0191106 A1 | 9/2004 | O'Neill et al. |
| 2004/0191292 A1 | 9/2004 | Chou |
| 2004/0193273 A1 | 9/2004 | Huang |
| 2004/0199260 A1 | 10/2004 | Pope et al. |
| 2004/0210274 A1 | 10/2004 | Bauhahn et al. |
| 2004/0210316 A1 | 10/2004 | King |
| 2004/0215173 A1 | 10/2004 | Kunst |
| 2004/0225360 A1 | 11/2004 | Malone |
| 2004/0249463 A1 | 12/2004 | Bindseil et al. |
| 2004/0258732 A1 | 12/2004 | Shikinami |
| 2004/0265350 A1 | 12/2004 | Sambrook |
| 2004/0267263 A1 | 12/2004 | May |
| 2005/0015059 A1 | 1/2005 | Sweeney |
| 2005/0015150 A1 | 1/2005 | Lee |
| 2005/0021084 A1 | 1/2005 | Lu et al. |
| 2005/0042288 A1 | 2/2005 | Koblish et al. |
| 2005/0049715 A1 | 3/2005 | Ito et al. |
| 2005/0049716 A1 | 3/2005 | Wagener et al. |
| 2005/0055099 A1 | 3/2005 | Ku |
| 2005/0058684 A1 | 3/2005 | Shanley et al. |
| 2005/0059972 A1 | 3/2005 | Biscup |
| 2005/0065609 A1* | 3/2005 | Wardlaw ............... A61F 2/441 623/17.12 |
| 2005/0085888 A1 | 4/2005 | Andreas et al. |
| 2005/0100470 A1 | 5/2005 | Lefebvre et al. |
| 2005/0100578 A1 | 5/2005 | Schmid et al. |
| 2005/0112397 A1 | 5/2005 | Rolfe et al. |
| 2005/0119753 A1 | 6/2005 | McGahan et al. |
| 2005/0125073 A1 | 6/2005 | Orban et al. |
| 2005/0137707 A1 | 6/2005 | Malek |
| 2005/0143822 A1 | 6/2005 | Paul |
| 2005/0159819 A1 | 7/2005 | McCormack et al. |
| 2005/0171611 A1 | 8/2005 | Stoy et al. |
| 2005/0175703 A1 | 8/2005 | Hunter et al. |
| 2005/0177238 A1 | 8/2005 | Khandkar et al. |
| 2005/0177247 A1 | 8/2005 | Canham et al. |
| 2005/0182494 A1 | 8/2005 | Schmid |
| 2005/0187555 A1 | 8/2005 | Biedermann et al. |
| 2005/0192669 A1 | 9/2005 | Zdeblick et al. |
| 2005/0197654 A1 | 9/2005 | Edman et al. |
| 2005/0202371 A1 | 9/2005 | McGuire |
| 2005/0220837 A1 | 10/2005 | Disegi et al. |
| 2005/0222688 A1 | 10/2005 | Zilla et al. |
| 2005/0228503 A1 | 10/2005 | Gundolf |
| 2005/0246032 A1 | 11/2005 | Bokros et al. |
| 2005/0271694 A1 | 12/2005 | Mansouri et al. |
| 2005/0272153 A1 | 12/2005 | Xuenong et al. |
| 2005/0273082 A1 | 12/2005 | Olsen |
| 2005/0273178 A1 | 12/2005 | Boyan et al. |
| 2005/0288795 A1 | 12/2005 | Bagga et al. |
| 2006/0002810 A1 | 1/2006 | Grohowski, Jr. |
| 2006/0015186 A1 | 1/2006 | Isaac |
| 2006/0047341 A1 | 3/2006 | Trieu |
| 2006/0057737 A1 | 3/2006 | Santini, Jr. et al. |
| 2006/0064170 A1 | 3/2006 | Smith et al. |
| 2006/0064172 A1 | 3/2006 | Trieu |
| 2006/0083730 A1 | 4/2006 | Kusanagi et al. |
| 2006/0093646 A1 | 5/2006 | Cima et al. |
| 2006/0100706 A1 | 5/2006 | Shadduck et al. |
| 2006/0100716 A1 | 5/2006 | Lerf |
| 2006/0105015 A1 | 5/2006 | Perla et al. |
| 2006/0111782 A1 | 5/2006 | Petersen |
| 2006/0111785 A1 | 5/2006 | O'Neil |
| 2006/0121609 A1 | 6/2006 | Yannas et al. |
| 2006/0129242 A1 | 6/2006 | Bergeron et al. |
| 2006/0141012 A1 | 6/2006 | Gingras |
| 2006/0149220 A1 | 7/2006 | Ullestad et al. |
| 2006/0149386 A1 | 7/2006 | Clark et al. |
| 2006/0173542 A1 | 8/2006 | Shikinami |
| 2006/0178744 A1 | 8/2006 | de Villiers et al. |
| 2006/0193885 A1 | 8/2006 | Leonard Neethling et al. |
| 2006/0195188 A1 | 8/2006 | O'Driscoll et al. |
| 2006/0200166 A1 | 9/2006 | Hanson et al. |
| 2006/0204581 A1 | 9/2006 | Gower et al. |
| 2006/0229715 A1 | 10/2006 | Istephanous et al. |
| 2006/0235534 A1 | 10/2006 | Gertzman et al. |
| 2006/0241593 A1 | 10/2006 | Sherman et al. |
| 2006/0264950 A1 | 11/2006 | Nelson et al. |
| 2006/0271022 A1 | 11/2006 | Steinbach et al. |
| 2006/0271201 A1 | 11/2006 | Kumar et al. |
| 2006/0276900 A1 | 12/2006 | Carpenter |
| 2006/0282166 A1 | 12/2006 | Molz et al. |
| 2006/0287689 A1 | 12/2006 | Debruyne et al. |
| 2006/0289388 A1 | 12/2006 | Yang et al. |
| 2006/0293757 A1 | 12/2006 | McKay et al. |
| 2007/0016163 A1 | 1/2007 | Santini, Jr. et al. |
| 2007/0026069 A1 | 2/2007 | Shastri et al. |
| 2007/0038299 A1 | 2/2007 | Stone et al. |
| 2007/0041952 A1 | 2/2007 | Guilak et al. |
| 2007/0043446 A1 | 2/2007 | Murray |
| 2007/0077267 A1 | 4/2007 | Molz, IV et al. |
| 2007/0105222 A1 | 5/2007 | Wolfinbarger et al. |
| 2007/0116734 A1 | 5/2007 | Akash |
| 2007/0123843 A1 | 5/2007 | Gill |
| 2007/0138042 A1 | 6/2007 | Wood |
| 2007/0141105 A1 | 6/2007 | Stein et al. |
| 2007/0141533 A1 | 6/2007 | Ford et al. |
| 2007/0150063 A1 | 6/2007 | Ruberte et al. |
| 2007/0150064 A1 | 6/2007 | Ruberte et al. |
| 2007/0150068 A1 | 6/2007 | Dong et al. |
| 2007/0160681 A1 | 7/2007 | Park et al. |
| 2007/0161986 A1 | 7/2007 | Levy |
| 2007/0162110 A1 | 7/2007 | Dave |
| 2007/0166348 A1 | 7/2007 | Van Dyke |
| 2007/0168021 A1 | 7/2007 | Holmes, Jr. et al. |
| 2007/0185580 A1 | 8/2007 | Posel |
| 2007/0185585 A1 | 8/2007 | Bracy et al. |
| 2007/0190880 A1 | 8/2007 | Dubrow et al. |
| 2007/0191963 A1 | 8/2007 | Winterbottom et al. |
| 2007/0196419 A1 | 8/2007 | Teller et al. |
| 2007/0202145 A1 | 8/2007 | Ghabrial et al. |
| 2007/0203584 A1 | 8/2007 | Bandyopadhyay et al. |
| 2007/0208420 A1 | 9/2007 | Ameer et al. |
| 2007/0213827 A1 | 9/2007 | Arramon |
| 2007/0233071 A1 | 10/2007 | Dewey et al. |
| 2007/0243225 A1 | 10/2007 | McKay |
| 2007/0250169 A1 | 10/2007 | Lang |
| 2007/0255262 A1 | 11/2007 | Haase |
| 2007/0255416 A1 | 11/2007 | Melkent et al. |
| 2007/0260320 A1 | 11/2007 | Peterman et al. |
| 2007/0270859 A1 | 11/2007 | Companioni |
| 2007/0293948 A1 | 12/2007 | Bagga et al. |
| 2008/0004704 A1 | 1/2008 | Katz |
| 2008/0015578 A1 | 1/2008 | Erickson et al. |
| 2008/0046082 A1 | 2/2008 | Lee |
| 2008/0065218 A1 | 3/2008 | O'Neil |
| 2008/0077247 A1 | 3/2008 | Murillo et al. |
| 2008/0109083 A1 | 5/2008 | Van Hoeck et al. |
| 2008/0119945 A1 | 5/2008 | Frigg |
| 2008/0147193 A1 | 6/2008 | Matthis et al. |
| 2008/0188940 A1 | 8/2008 | Cohen et al. |
| 2008/0200985 A1 | 8/2008 | Robie |
| 2008/0262622 A1 | 10/2008 | Butler |
| 2008/0288074 A1 | 11/2008 | O'Neil et al. |
| 2008/0306609 A1 | 12/2008 | Lee et al. |
| 2009/0005872 A1 | 1/2009 | Moumene et al. |
| 2009/0005874 A1 | 1/2009 | Fleischmann et al. |
| 2009/0024224 A1 | 1/2009 | Chen et al. |
| 2009/0030399 A1 | 1/2009 | Raiszadeh |
| 2009/0132051 A1 | 5/2009 | Moskowitz et al. |
| 2009/0222098 A1 | 9/2009 | Trieu et al. |
| 2009/0228109 A1 | 9/2009 | Pointillant et al. |
| 2009/0248162 A1 | 10/2009 | Peckham |
| 2009/0254182 A1 | 10/2009 | Kovarik et al. |
| 2009/0270986 A1 | 10/2009 | Christensen |
| 2009/0270988 A1 | 10/2009 | Snell et al. |
| 2009/0270991 A1 | 10/2009 | Michelson |
| 2009/0270992 A1 | 10/2009 | Gerber et al. |
| 2009/0276049 A1 | 11/2009 | Weiland |
| 2009/0281517 A1 | 11/2009 | Lambrecht et al. |
| 2009/0281625 A1 | 11/2009 | Enayati |
| 2009/0292363 A1 | 11/2009 | Goldfarb et al. |
| 2009/0317278 A1 | 12/2009 | Kokubo |
| 2009/0326657 A1 | 12/2009 | Grinberg et al. |

(56) References Cited

U.S. PATENT DOCUMENTS

| | | |
|---|---|---|
| 2010/0003639 A1 | 1/2010 | Salvi et al. |
| 2010/0016970 A1 | 1/2010 | Kapitan et al. |
| 2010/0042167 A1 | 2/2010 | Nebosky et al. |
| 2010/0042213 A1 | 2/2010 | Nebosky et al. |
| 2010/0042214 A1 | 2/2010 | Nebosky et al. |
| 2010/0042215 A1 | 2/2010 | Stalcup et al. |
| 2010/0042218 A1 | 2/2010 | Nebosky et al. |
| 2010/0042226 A1 | 2/2010 | Nebosky et al. |
| 2010/0076559 A1 | 3/2010 | Bagga et al. |
| 2010/0168798 A1 | 7/2010 | Clineff et al. |
| 2010/0190254 A1 | 7/2010 | Chian et al. |
| 2010/0234966 A1 | 9/2010 | Lo |
| 2010/0291286 A1 | 11/2010 | O'Neill et al. |
| 2011/0004307 A1* | 1/2011 | Ahn ................. A61F 2/4455 606/279 |
| 2011/0012280 A1 | 1/2011 | Deslauriers et al. |
| 2011/0064784 A1 | 3/2011 | Mullens et al. |
| 2011/0066244 A1 | 3/2011 | Frasier et al. |
| 2011/0071635 A1 | 3/2011 | Zhang et al. |
| 2011/0092948 A1 | 4/2011 | Shachar et al. |
| 2011/0137418 A1 | 6/2011 | O'Neil et al. |
| 2011/0153028 A1 | 6/2011 | Albertorio |
| 2011/0190888 A1 | 8/2011 | Bertele et al. |
| 2011/0190889 A1 | 8/2011 | Miller et al. |
| 2011/0224796 A1 | 9/2011 | Weiland et al. |
| 2011/0230970 A1 | 9/2011 | Lynn et al. |
| 2011/0313532 A1 | 12/2011 | Hunt |
| 2012/0303128 A1 | 11/2012 | Ullrich, Jr. et al. |
| 2012/0316650 A1 | 12/2012 | Ullrich, Jr. et al. |
| 2013/0030529 A1 | 1/2013 | Hunt |
| 2013/0190875 A1 | 7/2013 | Shulock et al. |
| 2014/0264995 A1 | 9/2014 | Lakshminarayanan et al. |
| 2015/0150689 A1 | 6/2015 | Wang et al. |
| 2015/0238324 A1 | 8/2015 | Nebosky et al. |
| 2015/0297349 A1 | 10/2015 | Butscher et al. |
| 2016/0280920 A1 | 9/2016 | Seto |
| 2017/0020685 A1 | 1/2017 | Geisler et al. |
| 2017/0056179 A1 | 3/2017 | Lorio |
| 2019/0053910 A1 | 2/2019 | Sansur et al. |
| 2019/0083275 A1 | 3/2019 | Bell et al. |
| 2019/0083282 A1 | 3/2019 | Roeder et al. |

FOREIGN PATENT DOCUMENTS

| | | |
|---|---|---|
| DE | 693 28 047 T2 | 3/2000 |
| DE | 19904436 A1 | 8/2000 |
| DE | 10051438 A1 | 5/2002 |
| DE | 695 28 346 T2 | 9/2002 |
| DE | 10120330 A1 | 11/2002 |
| DE | 10157315 C1 | 8/2003 |
| EP | 0617931 A2 | 10/1994 |
| EP | 0827726 A2 | 3/1998 |
| EP | 1 273 312 A2 | 1/2003 |
| EP | 1 287 851 A1 | 3/2003 |
| EP | 1475057 A1 | 11/2004 |
| EP | 1806112 A1 | 7/2007 |
| FR | 2697155 A1 | 4/1994 |
| JP | 6007388 A | 1/1994 |
| JP | 7116184 A | 5/1995 |
| JP | 8173463 A | 7/1996 |
| JP | 2587625 B2 | 12/1996 |
| JP | 2002325781 A | 11/2002 |
| JP | 2005329179 A | 12/2005 |
| WO | 03084602 A2 | 10/2003 |
| WO | 03101504 A1 | 12/2003 |
| WO | 2005/047467 A2 | 5/2005 |
| WO | 2006/088480 A2 | 8/2006 |
| WO | 2006/135727 A2 | 12/2006 |
| WO | 2007/135444 A2 | 11/2007 |

OTHER PUBLICATIONS

Office Action dated Sep. 24, 2010 in U.S. Appl. No. 11/060,377 (7 pages).

A. Cameron, entitled "Basic Lubrication Theory", Ellis Horwood Limited, pp. 134-137, 1976.

A. Cameron, entitled "The Principles of Lubrication", John Wiley and Sons Inc., pp. 542-559, 1966.

Office Action dated May 12, 2010 in U.S. Appl. No. 10/980,425 (22 pages).

Philip E. Mitchell, Handbook Editor, "Tool and Manufacturing Engineers Handbook", 4th Edition, vol. VIII Plastic Part Manufacturing, Society of Manufacturing Engineers, Dearborn, Michigan, pp. 2-17 and 2-18, 1996 (4 pages).

U.S. Appl. No. 60/149,027, filed Aug. 16, 1999 with U.S. Patent & Trademark Office (44 pages).

U.S. Appl. No. 08/200,636, filed Feb. 23, 1994 with U.S. Patent & Trademark Office (40 pages).

Office Action dated Apr. 17, 1995 in U.S. Appl. No. 08/200,636 (4 pages).

Supplemental Information Disclosure Statement dated Sep. 11, 1995 in U.S. Appl. No. 08/200,636 (7 pages).

U.S. Appl. No. 08/437,781, filed May 9, 1995 with U.S. Patent & Trademark Office (84 pages).

Office Action dated Nov. 1, 1996 in U.S. Appl. No. 08/437,781 (2 pages).

U.S. Appl. No. 09/639,612, filed Aug. 15, 2000 with U.S. Patent & Trademark Office (67 pages).

International Search Report for PCT/US2009/053751 dated Oct. 14, 2009.

International Preliminary Report on Patentability dated Feb. 15, 2011 for PCT/US2009/053724 (9 pages).

International Preliminary Report on Patentability dated Feb. 15, 2011 for PCT/US2009/053735 (8 pages).

International Preliminary Report on Patentability dated Feb. 15, 2011 for PCT/US2009/053751 (7 pages).

International Preliminary Report on Patentability dated Feb. 15, 2011 for PCT/US2009/053762 (5 pages).

International Preliminary Report on Patentability dated Mar. 1, 2011 for PCT/US2009/055380 (9 pages).

International Preliminary Report on Patentability dated Mar. 1, 2011 for PCT/US2009/055397 (10 pages).

Photos 309 and 310 show a poster of which Applicant is aware. By disclosing these photos, Applicant is making no statement as to whether or not these photos are material or are prior art relative to the present application.

Communication from Canadian Intellectual Property Office dated Jan. 11, 2013 for Canadian patent application No. 2,735,235 (2 pages).

Supplementary European Search Report dated Apr. 22, 2013 for European Application No. 09 80 7307 (7 pages).

Communication dated Apr. 11, 2013 from Canadian Intellectual Property Office for Canadian patent application No. 2,735,236 (3 pages).

Communication dated May 22, 2013 from European Patent Office for European Patent Application No. 09807307.5-1506 (1 page).

Communication dated May 2, 2013 from European Patent Office for European Patent Application No. 09807307.5-1506, including Supplementary European Search Report and opinion (7 pages).

Extended European Search Report dated Jun. 28, 2016 for European Application No. 16156901.7 (7 pages).

Extended European Search Report dated May 23, 2019 for European Application No. 19 15 3366 (8 pages).

International Search Report dated Sep. 28, 2009 of International Searching Authority for Application No. PCT/US2009/053724 (2 pages).

International Search Report dated Sep. 28, 2009 of International Searching Authority for Application No. PCT/US2009/053735 (2 pages).

International Search Report dated Sep. 23, 2009 of International Searching Authority for Application No. PCT/US2009/053762 (2 pages).

International Search Report dated Oct. 14, 2009 of International Searching Authority for Application No. PCT/US2009/053751 (2 pages).

(56) References Cited

OTHER PUBLICATIONS

International Search Report dated Apr. 13, 2010 of International Searching Authority for Application No. PCT/US2009/055380 (2 pages).
International Search Report dated Oct. 13, 2009 of International Searching Authority for Application No. PCT/US2009/055397 (2 pages).
Office Action dated Oct. 9, 2007 in U.S. Appl. No. 10/980,425 (16 pages).
Office Action dated Apr. 7, 2008 in U.S. Appl. No. 10/980,425 (20 pages).
Office Action dated Jul. 17, 2008 in U.S. Appl. No. 10/980,425 (3 pages).
Office Action dated Oct. 29, 2008 in U.S. Appl. No. 11/325,530 (11 pages).
Office Action dated Jun. 26, 2009 in U.S. Appl. No. 11/325,530 (13 pages).
Office Action dated Oct. 19, 2009 in U.S. Appl. No. 11/325,530 (6 pages).
Dr. Nicole Rotter, J. Aigner, A. Naumann, H. Planck, C. Hammer, G. Burmester, M. Sittinger; abstract of article entitled "Cartilage Reconstruction in Head and Neck Surgery: Comparison of Resorbable Polymer Scaffolds for Tissue Engineering of Human Septal Cartilage", in Journal of Biomedical Materials Research, vol. 42, Issue 3, pp. 347-356, Dec. 5, 1998; accessed on Oct. 25, 2010 at http://onlinelibrary.wiley.com/doi/10.1002/(SICI)1097-4636(19981205)42:3%3C347::AID-JBM2%3E3.0.CO;2-J/abstract.
Robert J. Klebe; article entitled "Cytoscribing: A Method for Micropositioning Cells and the Construction of Two- and Three-Dimensional Synthetic Tissues", Experimental Cell Research 179 (1988) 362-373, published by Academic Press, Inc.
Emanuel Sachs, Michael Cima, James Bredt, Alain Curodeau, Tailin Fan, and David Brancazio; article entitled "Cad-Casting: Direct Fabrication of Ceramic Shells and Cores by Three Dimensional Printing", Manufacturing Review vol. 5, No. 2, pp. 117-126, Jun. 1992, published by American Society of Mechanical Engineers.
Joseph P. Vacanti, Martin A. Morse, W. Mark Saltzman, Abraham J. Domb, Antonio Perez-Atayde, and Robert Langer; article entitled "Selective Cell Transplantation Using Bioabsorbable Artificial Polymers as Matrices", Journal of Pediatric Surgery, vol. 23, No. 1, pp. 3-9, Jan. 1988, published by Grune & Stratton, Inc.
N.R. Boeree, J. Dove, J.J. Cooper, J. Knowles, and G.W. Hastings, article entitled "Development of a Degradable Composite for Orthopaedic Use: Mechanical Evaluation of an Hydroxyapatite-Polyhydroxybutyrate Composite Material", Biomaterials, vol. 14, No. 10, pp. 793-796, 1993, published by Butterworth-Heinemann Ltd.
R.B. Martin, M.W. Chapman, N.A. Sharkey, S.L. Zissimos, B. Bay, and E.C. Shors, article entitled "Bone Ingrowth and Mechanical Properties of Coralline Hydroxyapatite 1 Yr After Implantation", Biomaterials, vol. 14, No. 5, pp. 341-348, 1993, published by Butterworth-Heinemann Ltd.
Article entitled "Fractal" (nine pages), published on the Internet by the online encyclopedia Wikipedia; downloaded from the internet on Dec. 14, 2006 in the United States from the following address: http://en.wikipedia.org/wiki/Fractals.
Editor in Chief Sybil P. Parker, p. 799 (showing entries from "fp" to "fracture test") of McGraw-Hill Dictionary of Scientific and Technical Terms, Fifth Edition, published by McGraw-Hill, Inc., 1994, New York.
Office Action dated Oct. 31, 2008 in U.S. Appl. No. 10/980,425 (20 pages).
Office Action dated Oct. 20, 2006 in U.S. Appl. No. 11/060,377 (10 pages).
Written Opinion dated Sep. 28, 2009 of International Searching Authority for Application No. PCT/US2009/053724 (8 pages).
Written Opinion dated Sep. 28, 2009 of International Searching Authority for Application No. PCT/US2009/053735 (7 pages).
Written Opinion dated Sep. 23, 2009 of International Searching Authority for Application No. PCT/US2009/053762 (4 pages).
Written Opinion dated Oct. 14, 2009 of International Searching Authority for Application No. PCT/US2009/053751 (6 pages).
Article entitled "Rolled Threads" (3 pages), published on the Internet by the online encyclopedia Wikipedia; downloaded from the internet on Aug. 24, 2009 in the United States from the following address: http://en.wikipedia.org/wiki/File:American_Machinists_Handbook-2e-p23-v001.png.
Written Opinion dated Apr. 13, 2010 of International Searching Authority for Application No. PCT/US2009/055380 (8 pages).
Written Opinion dated Oct. 13, 2009 of International Searching Authority for Application No. PCT/US2009/055397 (9 pages).
Unknown Author, article entitled "MacroPore Resorbable Technology: An Overview", Scientific Data Series in Resorbable Fixation, MKT004 Rev. Jun. 2001, pp. 1-8; distributed by Medtronic Sofamor Danek, 1800 Pyramid Place, Memphis TN 38132, (Jun. 2001).
Ralph E. Holmes, M.D., Stefan M. Lemperle, M.D., and Christopher J. Calhoun, M.B.A., article entitled "Protected Bone Regeneration", Scientific Data Series in Resorbable Fixation, MKT003 Rev. Jun. 2001, pp. 1-10; distributed by Medtronic Sofamor Danek, 1800 Pyramid Place, Memphis TN 38132, (Jun. 2001).
D.R. Sumner, T.M. Turner, R.M. Urban, R.M. Leven, M. Hawkins, E.H. Nichols, J.M. Mcpherson, J.O. Galante, article entitled "Locally Delivered rhTGF-B2 Enhances Bone Ingrowth and Bone Regeneration at Local and Remote Sites of Skeletal Injury", Journal of Orthopaedic Research 19 (2001) pp. 85-94, published by Elsevier Science Ltd.
International Search Report dated May 18, 2005 of International Searching Authority for Application No. PCT/US2004/036997 (3 pages).
U.S. Appl. No. 08/048,408, filed Apr. 15, 1993 with U.S. Patent & Trademark Office (108 pages).
Preliminary Amendment dated Jul. 8, 1993 and filed in U.S. Appl. No. 08/048,408 with U.S. Patent & Trademark Office (12 pages).
Machine English translation of JP 2587625 (10 pages).
International Preliminary Report on Patentability dated May 8, 2006 of International Searching Authority for Application No. PCT/US2004/036997 (6 pages).
Written Opinion dated May 18, 2005 of International Searching Authority for Application No. PCT/US2004/036997 (5 pages).
Communication and supplementary European search report dated Nov. 14, 2008 from European Patent Office in application No. 04818642 (3 pages).
Office Action dated Jun. 25, 2010 from European Patent Office in application No. 04818642 (5 pages).
International Search Report dated Mar. 12, 2007 of International Searching Authority for PCT/US2005/019045 (3 pages).
International Preliminary Report on Patentability dated Aug. 21, 2007 of International Searching Authority for Application No. PCT/US2005/019045 (7 pages).
Written Opinion dated Mar. 12, 2007 of International Searching Authority for Application No. PCT/US2005/019045 (6 pages).
Office Action dated May 7, 2007 in U.S. Appl. No. 11/060,377 (13 pages).
Office Action dated Aug. 20, 2007 in U.S. Appl. No. 11/060,377 (3 pages).
Office Action dated Feb. 20, 2008 in U.S. Appl. No. 11/060,377 (5 pages).
Office Action dated Sep. 2, 2008 in U.S. Appl. No. 11/060,377 (7 pages).
Office Action dated Dec. 15, 2008 in U.S. Appl. No. 11/060,377 (8 pages).
Interview Summary dated Mar. 5, 2009 in U.S. Appl. No. 11/060,377 (2 pages).
Office Action dated May 27, 2009 in U.S. Appl. No. 11/060,377 (7 pages).

* cited by examiner

ORTHOPAEDIC IMPLANT WITH POROUS STRUCTURAL MEMBER

CROSS REFERENCE TO RELATED APPLICATIONS

This is a division of U.S. patent application Ser. No. 15/878,723 entitled "ORTHOPAEDIC IMPLANT WITH POROUS STRUCTURAL MEMBER," filed Jan. 24, 2018, which is incorporated herein by reference. U.S. patent application Ser. No. 15/878,723 is a continuation-in-part application based on U.S. patent application Ser. No. 15/626,596 entitled "ORTHOPAEDIC IMPLANT WITH POROUS STRUCTURAL MEMBER," filed Jun. 19, 2017, which is incorporated herein by reference. U.S. patent application Ser. No. 15/626,596 is a division of U.S. patent application Ser. No. 14/637,142 entitled "ORTHOPAEDIC IMPLANT WITH POROUS STRUCTURAL MEMBER", filed Mar. 3, 2015, which has now issued as U.S. Pat. No. 9,700,431 and which is incorporated herein by reference. U.S. patent application Ser. No. 14/637,142 is a continuation-in-part application based upon U.S. patent application Ser. No. 12/540,515, entitled "ORTHOPAEDIC IMPLANT WITH POROUS STRUCTURAL MEMBER", filed Aug. 13, 2009, which is incorporated herein by reference. U.S. patent application Ser. No. 12/540,515 is based upon U.S. provisional patent application Ser. No. 61/088,460, entitled "SPINAL DEVICES", filed Aug. 13, 2008, which is incorporated herein by reference.

BACKGROUND OF THE INVENTION

1. Field of the Invention

The present invention relates to orthopaedic devices, and, more particularly, to orthopaedic implants.

2. Description of the Related Art

Most orthopaedic implants are formed from a metallic material suitable for a given implant, such as a hip implant, knee implant, glenoid implant, etc. In the case of articulating joints, the implant may include a non-metallic load bearing surface, such as an ultra high molecular weight polyethylene (UHMWPE). The UHMWPE is attached to the metallic body of the implant, and provides the implant with good wear characteristics and low friction.

It is also known to provide an implant with a porous bony ingrowth surface. For example, a hip implant may include a porous surface on the stem which is intended to allow bony ingrowth of the proximal end of the femur bone. Such a porous surface may be in the form of a metal porous surface which is bonded, such as by heat sintering, to the stem of the implant. Examples of porous surfaces of this type include a woven mesh, a fiber mesh and particles. Knee implants are also known that include porous ingrowth surfaces that can bear load from surrounding anatomic structures.

Porous surfaces of the type described above which are used with implants are not typically part of a single structural member with two opposed, external porous surfaces. For example, in a knee implant, the distal surface of the implant can sit on the porous material that is slightly above the substrate material, but the porous material only typically has one external surface for tissue ingrowth. For hip implants, the porous ingrowth surface is usually provided as a coating on a structural component of the implant, such as the stem.

In some orthopaedic applications, such as spinal cages, it is beneficial to have a porous member that extends between two external, load bearing surfaces of the implant. In such arrangements, a cavity is typically formed between the two external surfaces of the implant and filled with a porous ingrowth material, which is typically a natural substance such as cancellous bone tissue. Such an implant is described in U.S. Patent Application No. 2002/0091447 to Shimp et al. One problem with the implant described by Shimp et al. is that harvesting sufficient cancellous bone tissue to fill the cavity is expensive, and host rejection issues can be a concern. Other similar implants that contemplate utilizing natural or synthetic materials are described in U.S. Patent Application Publication No. 2004/0210316 to King et al., and U.S. Pat. No. 6,423,095 to Van Hoeck et al. In each of these described implants, the porous material held in the cavity is fairly isolated from bearing load from surrounding anatomic structures after implantation, with external surfaces that are either flush or below the most protruding external surface of the main implant body. This is intentional, as the materials placed in the cavity tend to have significantly lower strength than the implant body. However, isolating the porous ingrowth material from bearing loads from surrounding anatomic structures also decreases the amount of surface area the porous ingrowth material has in contact with the anatomic structures, which can slow down integration of the implant. In addition, the porous materials placed in the cavity are typically resorbable by the body and will not last throughout the life of the implant.

Porous materials in a cavity of an implant may be loaded with one or more types of biological agents, to assist with the healing of nearby anatomical structures or tissues, or to protect against infections, or to fight disease, via the absorption of the agent by the surrounding tissue via the pores of the porous material. However, problems exist with expulsion of the agent from the pores after loading the porous material with the agent and prior to implantation of the implant, and of leakage of the agent through the opening via which the implant was initially loaded, particularly if the agent was loaded into the implant after the implant was positioned in the body.

What is needed in the art is an orthopaedic implant and associated devices and methods that can overcome some of the disadvantages of known implants and methods.

SUMMARY OF THE INVENTION

In accordance with an aspect of the present invention, there is provided a tool configured for use with an orthopaedic implant. The orthopaedic implant includes an implant body having a first surface, a second surface opposite the first surface, a cavity formed therein that extends through the first surface and the second surface, the implant body being substantially non-porous and further including a third surface with at least one first opening formed therethrough to the cavity and at least one second opening, the at least one first opening comprising an threaded outer portion having an outer diameter and an threaded inner portion having an inner diameter, the outer diameter greater than the inner diameter. The implant further includes a load bearing member including a substantially porous material held within the cavity, the load bearing member configured to receive, via the at least one first opening, a material agent, the load bearing member having a first contact surface extending out of the cavity past the first surface. The tool includes a tubular assembly having a tubular passage including a first end and a second end, the first end having a means for attachment to the implant body, a plug, and a plunger coupled to the plug. The tubular passage is configured to receive, via the second end, the material agent and the plunger coupled to the plug. The plunger coupled to the plug is configured to slide through the tubular passage for expelling the material agent from the tubular passage into the load bearing member via the at least one first opening. The plunger coupled to the plug is also configured to rotate within the tubular passage for coupling the plug with the first opening to seal the first opening against expulsion of the material agent from the load bearing member via the first opening.

In accordance with an aspect of the present invention, there is provided a method of charging an orthopaedic implant with a material agent. The orthopaedic implant includes an implant body having a first surface, a second surface opposite the first surface, a cavity formed therein that extends through the first surface and the second surface, the implant body being substantially non-porous and further including a third surface with at least one first opening formed therethrough to the cavity and at least one second opening, the at least one first opening comprising an threaded outer portion having an outer diameter and an threaded inner portion having an inner diameter, the outer diameter greater than the inner diameter. The implant further includes a load bearing member including a substantially porous material held within the cavity, the load bearing member configured to receive, via the at least one first opening, a material agent, the load bearing member having a first contact surface extending out of the cavity past the first surface. The method includes coupling a tubular assembly to the third surface of the implant body, wherein the tubular assembly includes a tubular passage having a first end and a second end, and wherein the first end is coupled to the third surface such that said tubular passage is centered on the at least one first opening, placing the material agent into the tubular passage via the second end, sliding a plunger coupled to a plug through the tubular passage via the second end, thereby expelling the material agent from the tubular passage into the load bearing member via the at least one first opening, and rotating the plunger within the tubular passage for coupling the plug with the at least one first opening for sealing the at least one first opening against expulsion of the material agent from the load bearing member via the first opening.

An advantage of the present invention is that the orthopaedic implant can be initially charged with a material agent before or after the implant is placed in the body, or re-charged with the material agent during a second surgical procedure.

Another advantage of the present invention is that one or more openings of the orthopaedic implant, through which the implant is charged with the material agent, can be sealed against leakage or expulsion of the material agent from the implant.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

The exemplifications set out herein illustrate embodiments of the invention, and such exemplifications are not to be construed as limiting the scope of the invention in any manner.

DETAILED DESCRIPTION OF THE INVENTION

I. Porous Spinal Devices—Laminate Designs

The present invention provides a laminate method for a spinal implant or implant component, including manufacturing methods for sheet creation, bonding/assembly methods, and ways of creating tapers. Further, the present invention provides delivery of therapeutic agents through a spinal device.

The present invention addresses these issues by providing the design and method of manufacturing of a porous spinal fusion device.

A. Materials

Material options for the spinal device include the following: implantable polymers (such as PEEK, PMMA), implantable reinforced polymers (such as carbon-fiber reinforced PEEK), implantable metals (such as titanium, titanium alloy), and implantable ceramics (such as hydroxyapatite, alumina). One or more of these materials can be combined in a given device.

B. Overall Design

Figure 1:
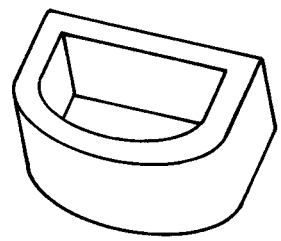
FIG. 1 is a perspective view of an embodiment of a solid component of a device formed according to the present invention.
Figure 2:
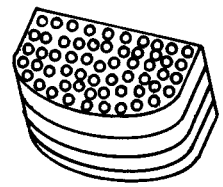
FIG. 2 is a perspective view of an embodiment of a porous component of a device formed according to the present invention.
Figure 3:
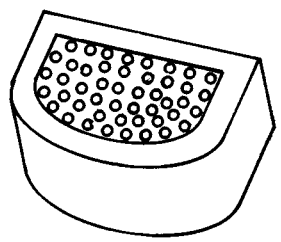
FIG. 3 is a perspective view of a device created from the solid component shown in FIG. 1 and the porous component shown in FIG. 2.

With regard to the overall design, the implant can include entirely porous material or one or more porous regions and one or more solid regions. Additionally, an entirely porous device can be created to mate with existing solid devices (See FIGS. 1-3).

The porous region is created by stacking layers of material with interconnecting holes/geometry (hereafter referred to as holes).

Figure 4:
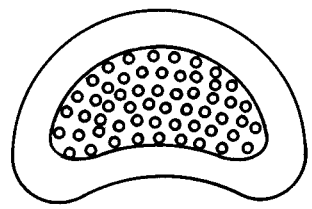
FIG. 4 is a cross-sectional view of a single, continuous layer with porous and solid regions.

The solid region can be formed by traditional techniques such as injection molding or machining or by bonding solid sheets together. The later method allows the solid and porous regions to be created from continuous sheets (See FIG. 4).

The holes in the sheets can be created by, for example, laser cutting, punching, etching, electrical discharge machining, plasma etching, electroforming, electron beam machining, water jet cutting, stamping, or machining. For polymer based materials, they can be created as the sheets are created by, for example, extruding, injection molding, or hot stamping.

Attachment of the sheets to each other can be achieved by any number of ways, including the following:

1. Heat. Heat can be generated by several ways:
   a. Ultrasonic welding—use ultrasonic waves to create heat at the interface of layers.
   b. Heat staking—use a heated tool to cause melting between the layers
   c. Vibratory welding
   d. Laser welding
   e. Convection—use an oven to create heat to cause bonding
   f. Intermediary layer—for example, use a material that can absorb energy waves that pass through the polymer (for example PEEK) without causing damage. The absorbed energy will cause localized heating. An example of such a coating is Clearweld by Gentex® Corporation. The laser waves that Clearweld absorbs pass through the PEEK without causing damage, allowing the layers to be melted together without large scale damage to the PEEK.
2. Chemical.
   a. Adhesives—a secondary material (such as adhesive) can be used to bond the material.
   b. Solvent bonding—a material in which the polymer or reinforced polymer is soluble can be applied to the sheet surfaces allowing multiple surfaces to be bonded to one another.
   c. Overmolding—overmolding of the polymer or reinforced polymer can provide a chemical bonding
3. Mechanical.
   a. Overmolding—overmolding of a polymer or reinforced polymer can create a mechanical lock between components on a micro or macro scale (microscale—the molded material locks with surface asperities of the existing material. Macroscale—features such as tongue-groove connections or undercuts). The overmolded material can be a separate component from the layers or one layer can be overmolded onto another layer.
   b. Features are provided within the layers or by a separate component which provides a mechanical lock—e.g. A pin, snap lock connection, dove-tail, tongue-groove, rivet, screw and/or melting tabs to create a mechanical lock. For example, one or more rivets can connect all layers of a porous implant together. These connection features can be made of any implantable material including, but not limited to, titanium, titanium alloy, PEEK, and/or other implantable polymers. These features can also be used as radiopaque markers as is described below.
   c. Some adhesives provide a mechanical bond in addition to or instead of a chemical bond.

4. Combinations of any/all of the above methods.

If the porous and solid regions are created separately (as in FIGS. 1-3), it may be desirable to bond the two together. There are several methods of achieving this bond:

1. Heat. Heat can be generated by several ways:
   a. Ultrasonic welding—use ultrasonic waves to create heat at the interface of layers.
   b. Heat staking—use a heated tool to cause melting between the layers
   c. Vibratory welding
   d. Laser welding
   e. Convection—use an oven to create heat to cause bonding
   f. Intermediary layer—for example, use a material that can absorb energy waves that pass through the polymer (for example PEEK) without causing damage. The absorbed energy will cause localized heating. An example of such a coating is Clearweld by Gentex® Corporation. The laser waves that Clearweld absorbs pass through the PEEK without causing damage, allowing the layers to be melted together without large scale damage to the PEEK.
2. Chemical.
   a. Adhesives—a secondary material (such as adhesive) can be used to bond the material.
   b. Solvent bonding—a material in which the polymer or reinforced polymer is soluble can be applied to the sheet surfaces allowing multiple surfaces to be bonded to one another.
   c. Overmolding—overmolding of the polymer or reinforced polymer can provide a chemical bonding
3. Mechanical.
   a. Overmolding—overmolding of a polymer or reinforced polymer can create a mechanical lock between components on a micro or macro scale (microscale—the molded material locks with surface asperities of the existing material. Macroscale—features such as tongue-groove connections or undercuts). The overmolded material can be a separate component from the layers or one layer can be overmolded onto another layer.
   b. Features are provided within the layers or by a separate component which provides a mechanical lock—e.g. A pin, snap lock connection, dove-tail, tongue-groove, rivet, and/or melting tabs to create a mechanical lock. For example, the porous material can attach to the windows that are typical in spinal cages or to a groove or ledge is created along the interior edge of the solid ring (see FIGS. 5-10). These connection features can be made of any implantable material including, but not limited to, titanium, titanium alloy, PEEK, and/or other implantable polymers. These features can also be used as radiopaque markers as is discussed later in this disclosure.
   c. Some adhesives provide a mechanical bond in addition to or instead of a chemical bond.
4. Combinations of any/all of the above methods.

Assembly of layer to layer or one component to another (for example a porous component to a solid component) can be aided by such ways as surface modifications to improve adhesive or solvent bonding or roughened surfaces.

Figure 5:
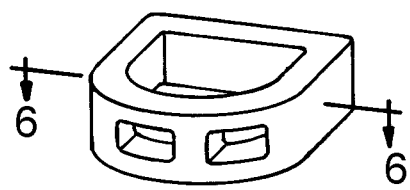
FIG. 5 is a perspective view of an embodiment of a spinal cage with windows.
Figure 6:
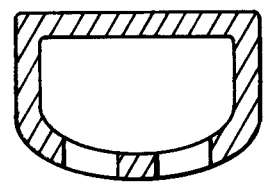
FIG. 6 is a cross-sectional view of the spinal cage shown in FIG. 5 taken along line 6-6.

FIGS. 5-6 illustrate a spinal cage showing windows (a cross section view is shown at the right). This is an example of a type of feature onto which the porous component can be bonded.

Figure 7:
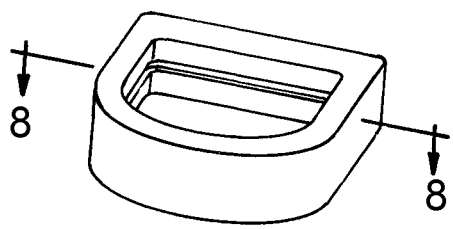
FIG. 7 is a perspective view of an embodiment of a spinal cage with a ledge or groove.
Figure 8:
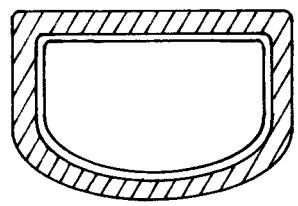
FIG. 8 is a cross-sectional view of the spinal cage shown in FIG. 7 taken along line 8-8.

FIGS. 7-8 illustrate a spinal cage showing a ledge or groove (a cross section view is shown at the right). This is an example of a type of feature onto which the porous component can be bonded.

Figure 9:
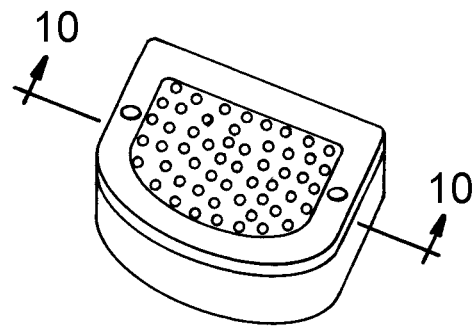
FIG. 9 is a perspective view of an embodiment of a spinal cage with a two-part solid component that is assembled to contain the porous material.
Figure 10:
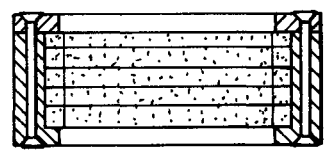
FIG. 10 is a cross-sectional view of the spinal cage shown in FIG. 9 taken along line 10-10.

FIGS. 9-10 illustrate a spinal cage showing a two-part solid component that is assembled to contain the porous material. In this example mechanical means (screw/rivet) are used in conjunction with an adhesive bond. Adhesive ways alone, mechanical ways alone or any of the other manufacturing methods discussed in this disclosure are also options.

Figure 11:
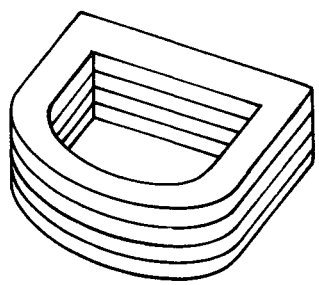
FIG. 11 is a perspective view of an embodiment of a spinal cage with laminates perpendicular to an axis of the spinal cage.
Figure 12:
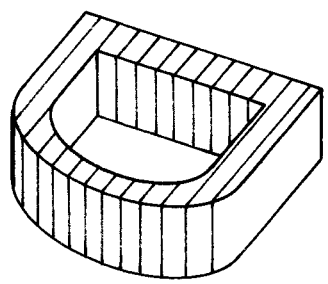
FIG. 12 is a perspective view of an embodiment of a spinal cage with laminates parallel to an axis of the spinal cage.
Figure 13:
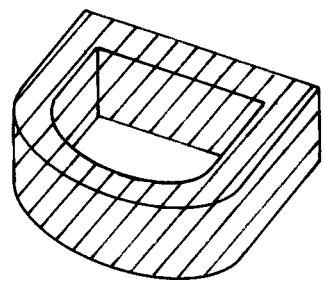
FIG. 13 is a perspective view of an embodiment of a spinal cage with laminates at an angle to an axis of the spinal cage.
Figure 14:
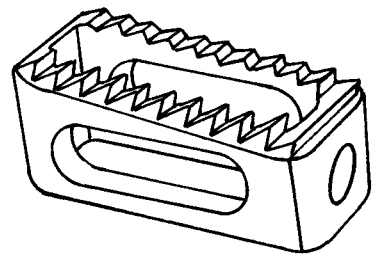
FIG. 14 is a perspective view of an embodiment of a spinal cage.
Figure 15:
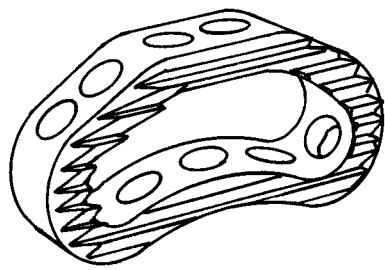
FIG. 15 is a perspective view of another embodiment of a spinal cage.
Figure 16:
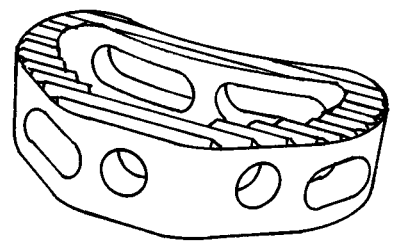
FIG. 16 is a perspective view of yet another embodiment of a spinal cage.
Figure 17:
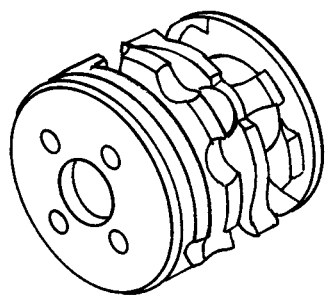
FIG. 17 is a perspective view of yet another embodiment of a spinal cage.

FIGS. 11-13 illustrate a spinal cages showing laminates perpendicular, parallel, and at an angle to the axis of the implant.

The laminate portion of the implant can have layers oriented in any direction. For example, the layers can be perpendicular, parallel, or at an angle to the axis of the implant (See FIGS. 11-13). This angle need not be constant within an implant.

The overall shape of the implant can be of any typical existing type, such as ALIF, TLIF, PLIF, and standard round cages (see FIGS. 14-17)

C. Delivery of Therapeutic Agent.

Figure 18:
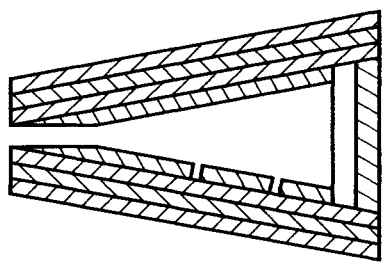
FIG. 18 is a sectional view of an implant with features for the delivery of therapeutic agents.

This device can be used to deliver therapeutic agents directly to the tissue surrounding the implant (See FIG. 18). Some examples of situations in which this would be desired: delivery of oncology treatments to cancerous tissue or tissue surrounding cancerous tissue; delivery of agents (such as BMP, hydroxyapatite slurry, and/or platelets) to encourage/enhance bone growth to promote faster and better fusion; and delivery of analgesic agents to reduce pain. This list is not exhaustive.

FIG. 18 illustrates a sectioned, side-view of an implant with features for the delivery of therapeutic agents.

The implant can include a reservoir for delivery of the therapeutic agent over an extended period of time. Openings leading from the reservoir to the porous material allow for controlled release of the therapeutic agents at a desired rate. The reservoir can be refilled at any time before, during, or after the surgery.

If immediate delivery of the therapeutic agents to the surrounding tissue is all that is required (not extended time release), the design need not include a reservoir. In this case, the therapeutic agents can be directly routed from the implant access to the porous material via channels. However, a reservoir can be included in an immediate delivery design; the openings in the reservoir would be sized to allow for immediate release of the therapeutic agent rather than a slower, long-term delivery.

The access in the implant (see FIG. 18) can mate with an insertion of a delivery tool (such as a needle) or a device (or catheter leading to a device) to allow for remote filling of the reservoir (such as by way of a subcutaneous port or external pain-pump).

In order to allow and promote bone growth through the implant from one vertebra to the other, openings run from the superior to the inferior portion of the implant and be appropriately sized to allow for bone ingrowth (See FIG. 18).

D. Anterior-Posterior Taper

Figure 19:
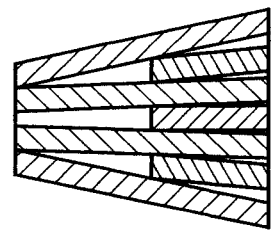
FIG. 19 is a sectional view of a tapered implant.
Figure 20:
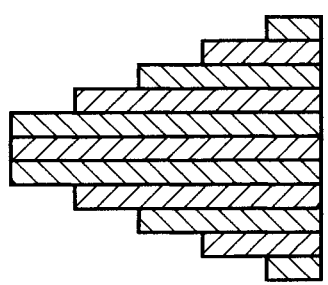
FIG. 20 is a sectional view of another tapered implant.
Figure 21:
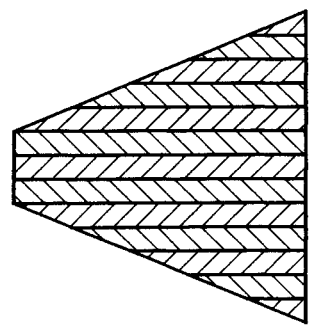
FIG. 21 is a sectional view of yet another tapered implant.
Figure 22:
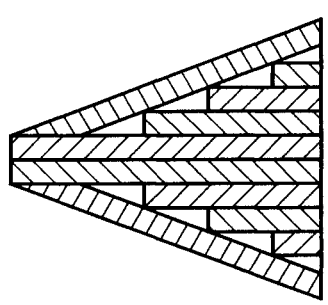
FIG. 22 is a sectional view of yet another tapered implant.
Figure 23:
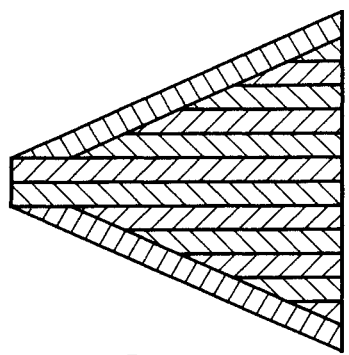
FIG. 23 is a sectional view of yet another tapered implant.

Some implants are tapered to mate with the natural anterior-posterior taper that exists between vertebrae. If a solid portion exists, this taper can be created by traditional machining and/or molding techniques. In the porous region, there are several ways of creating this taper, including the following:

a. If the design includes a reservoir, the reservoir itself can be tapered. The porous ingrowth layers can be of uniform thickness and layered outside of the reservoir (as indicated in FIG. 18).

b. A wedge-shaped piece or pieces can create the taper with the ingrowth layers stacked on the wedge(s). This is essentially the same design as shown in FIG. 20 without the reservoir, access and holes for the therapeutic agent delivery. To allow and promote bone growth through the implant from one vertebra to the other, openings run from the superior to the inferior portion of the implant and be appropriately sized to allow for bone ingrowth (See FIG. 18).

c. Shorter layers can be stacked with larger layers to create an overall taper as in FIG. 19.

d. Layers of varying lengths can be sacked to create a stepped taper as in FIG. 20.

e. Similar to the technique in (d), layers of varying length can be stacked. A smooth taper can be created by using layers that are tapered prior to stacking or the smooth taper can be created, by such ways as machining or hot forming, after the layers are stacked. The second of these would involve first creating a part like that in (d), then removing material to create the smooth taper shown in FIG. 21.

f. Another way of creating a smooth surface on a stepped taper is to have one or more outer layers which are parallel to the taper face, as shown in FIG. 22.

g. The design in (f) does not allow for a large amount of contact area between the outer layer of the taper and the corners of the stepped layer. One way of providing increased contact area (which can provide increased strength) is to taper the stepped layers as in FIG. 21 before adding the outer layer(s) that are parallel to the face of the taper. An example of this is shown in FIG. 23.

E. Interface with Bone

It is often desirable to have an implant-bone interface with relative high friction. Traditionally, this is achieved by such ways as a roughened implant surface, teeth (See FIGS. 24-25), spikes, or hooks.

In a laminate implant, there are several options for creating such features. These options include the following:

a. Form features prior to bonding laminate sheets: Form teeth or other "rough" features into the outermost layers of the implant prior to bonding them to the other sheets. These teeth can be created by several ways:
   i. Form material—for example: heat forming, cold forming.
   ii. Remove material—for example: machining, laser cutting, chemical etching.
   iii. Add material—attach material to create the features by, for example, insert molding, mechanical attachment, adhesive bonding, laser welding, solvent bonding.

b. Form features after bonding laminate sheets: Form the rough surface features on the faces of the implant after the sheets have been bonded. These features can be formed by the same ways as listed in (a).

c. Secondary feature (such as hooks, spikes, etc) protruding from the implant into the bone. This feature can be attached by, for example, insert molding, mechanical attachment, adhesive bonding, laser welding, or solvent bonding.

Figure 24:
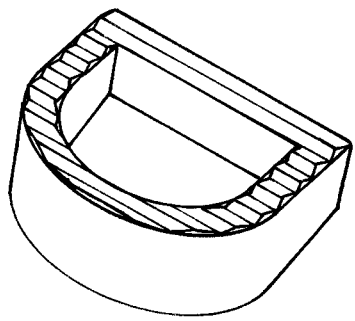
FIG. 24 is a perspective view of an implant showing teeth that mate with surrounding bone.
Figure 25:
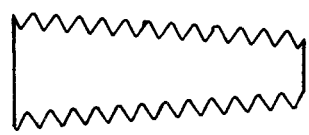
FIG. 25 is a side view of the implant shown in FIG. 24.

FIGS. 24-25 illustrate an implant showing teeth that mate with the surrounding bone.

F. Interface with Instruments

To aid in insertion of the implant into position in the body, it is often necessary to attach the implant to instrumentation. The material near the interface of the instrument and implant can often see additional stress. In a partially or fully laminate implant, it may be necessary to provide additional support in the region of this interface. This can be achieved by a number of ways, including: designing the instrument to reduce stresses and/or strengthening the implant in the region of the interface. For example, in the case of an instrument that contains a male thread which mates with a female thread in the implant, the implant can be strengthened by adding metal, solid polymer, or reinforced polymer in the region of the female thread. In machine design, thread inserts are frequently used to repair damaged threads. In this case, thread inserts can be used to strengthen the implant at the interface with the instrument(s).

G. Radiopaque Markers

When a radiolucent material, such as unfilled PEEK, is used, it is sometimes desirable to have the ability to see some or all of that implant on a diagnostic tool such as x-ray without the white-out problems of solid metal. For example, the surgeon may use such markers to determine the orientation and position of the implant to ensure proper placement during surgery. Radiopaque markers can provide this ability. The opacity and/or amount of radiopaque material can be controlled so that the marker does not prevent evaluation of the tissue near the implant by x-ray or other diagnostic ways. Material options include, but are not limited to, the following:

a. Implantable metals (stainless steel, titanium, or titanium alloys for example).

b. Barium sulfate filled PEEK.

c. Carbon filled PEEK.

d. Other polymers with radiopaque material (such as barium sulfate or zirconium dioxide).

Examples of the marker design include one or more of the following:

a. One or more radiopaque pins.

b. Assembly features such as rivets or pins.

c. Coating a portion of the device with a radiopaque material. Examples of methods for creating a radiopaque coating include, but are not limited to, the following:
   i. Using chemical vapor deposition to deposit a layer of titanium onto the polymer.
   ii. Using a radiopaque ink such as Radiopaque™ ink (developed by CI Medical).

d. One or more of the laminate layers being radiopaque. Examples of methods to make the layer(s) radiopaque include, but are not limited to, the following:
   i. Making the layer from an implantable metal (such as tantalum, titanium, titanium alloy, cobalt chrome, or stainless steel).
   ii. Using a barium sulfate filled polymer to create the layer.
   iii. Coating the layer with a radiopaque material—for example, using chemical vapor deposition to deposit a layer of titanium onto the surface of one or more layers.

e. A slightly radiopaque porous material. This can be achieved, for example, by using a polymer with barium sulfate.

II. Porous Polymer Spinal Fusion Devices

The key to the success of a spinal fusion surgery is the formation of good bone growth between the vertebrae that are being fused. Evaluation of this bone growth is, thus, critical to determining the progress and eventual success of the surgery.

Existing porous spinal cages are made of biocompatible metals. Due to the density of these metals, the implants made post-operative examination of the tissue surrounding the implant difficult.

Several current devices are now made from solid biocompatible polymers such as PEEK. PEEK is a relatively radiolucent material. While this addresses the issue of radiopacity for solid fusion devices, it is often desired to encourage more rapid bone growth between the two vertebrae.

One solution for this problem is implants made from porous biocompatible polymers, such as PEEK or reinforced porous PEEK.

A. Overall Design

Such implants can be entirely porous or have a mix of porous and solid polymer. For example, a solid ring of material can surround a porous core (See FIG. 26).

Figure 26:
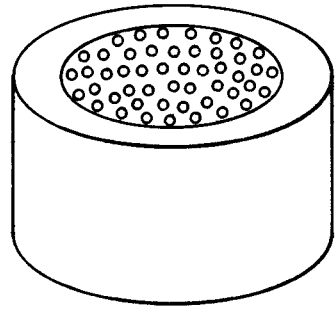
FIG. 26 is a spinal fusion device.

FIG. 26 illustrates a spinal fusion device with solid region (Region 1) and porous region (Region 2)

One embodiment of the design is a porous center component that mates with existing solid, ring-like devices. This device could be assembled with the solid device in a manufacturing setting or in the operating room.

If a solid region/component exists, the porous and solid regions may need, but do not necessarily need, to be attached to one another. Examples of methods that can be used to attach the porous and solid material are:
  a. Mechanical features—snap-fit connections, 'dove-tail' types of connections.
  b. Adhesive bonding.
  c. Solvent bonding.
  d. Heat applied by, for example, laser, ultrasonic or vibratory welding, convection heating, heat staking.

B. Material
  a. Method of creating porosity
    i. Laminate design—bonding sheets of material which contain holes.
    ii. Foaming methods.
    iii. Bond 'beads' of polymer—bead of any shape can be bonded together (via, for example, heating, adhesive bonding, or solvent bonding) to create a porous structure.
    iv. Mix of polymer and dissolvable material.
      1. One method involves creating a mixture of powdered implantable material (e.g. PEEK) and a powder (e.g. salt) that is soluble in something in which the implantable material is not soluble (such as water, isopropyl alcohol for the PEEK example). The mixture is then heated to bond the implantable particles together. Pressure can also be applied to aid in the bonding of particle to particle. Heat can be created by convection or other ways (such as coating the powder with a material that absorbs a given range of energy waves—such as laser waves—and causes heating. E.g. Clearweld coating by Gentex® Corporation). Finally, dissolve away the filler to create the porous implantable material. This method can create net shape parts or raw material shapes from which individual parts can be created.
      2. Another method involves mixing an implantable polymer with a dissolvable material such as described above. The mixture is then pelletized and then injection molded to an intermediary or the final part shape. The filler is dissolved away to create the porous implantable polymer.
  b. Reinforcement—If improved mechanical properties are desired, various reinforcing materials can be used. For example, carbon fiber or barium sulfate can be used.

C. Radiopaque Markers

It is sometimes desirable to have the ability to see some of the implant on a diagnostic tool such as an x-ray without the white-out problems of solid metal. For example, the surgeon may use such markers to determine the orientation and position of the implant to ensure proper placement during surgery. Radiopaque markers can provide this ability. The opacity and/or amount of radiopaque material can be controlled so that the marker does not prevent evaluation of the tissue near the implant by x-ray or other diagnostic ways. Material options include, but are not limited to, the following:
  a. Implantable metals (stainless steel, titanium, or titanium alloys for example).
  b. Barium sulfate filled PEEK.
  c. Carbon filled PEEK.
  d. Other polymers with radiopaque material (such as barium sulfate or zirconium dioxide).

Examples of the marker design include one or more of the following:
  a. One or more radiopaque pins.
  b. Coating a portion of the device with a radiopaque material. Examples of methods for creating a radiopaque coating include, but are not limited to, the following:
    i. Using chemical vapor deposition to deposit a layer of titanium onto the polymer.
    ii. Using a radiopaque ink such as Radiopaque™ ink (developed by CI Medical).
  c. A slightly radiopaque porous material. This can be achieved, for example, by using a polymer with barium sulfate.

Figure 27:
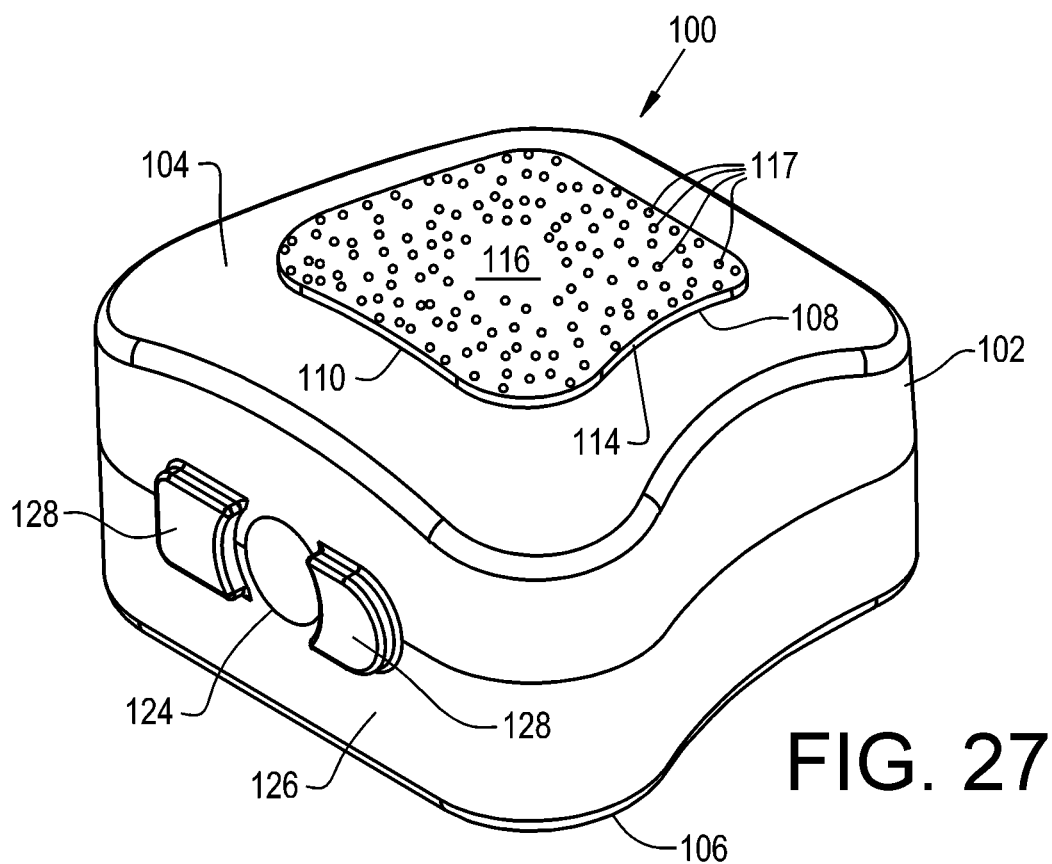
FIG. 27 is a perspective view of another embodiment of an orthopaedic implant according to the present invention.
Figure 28:
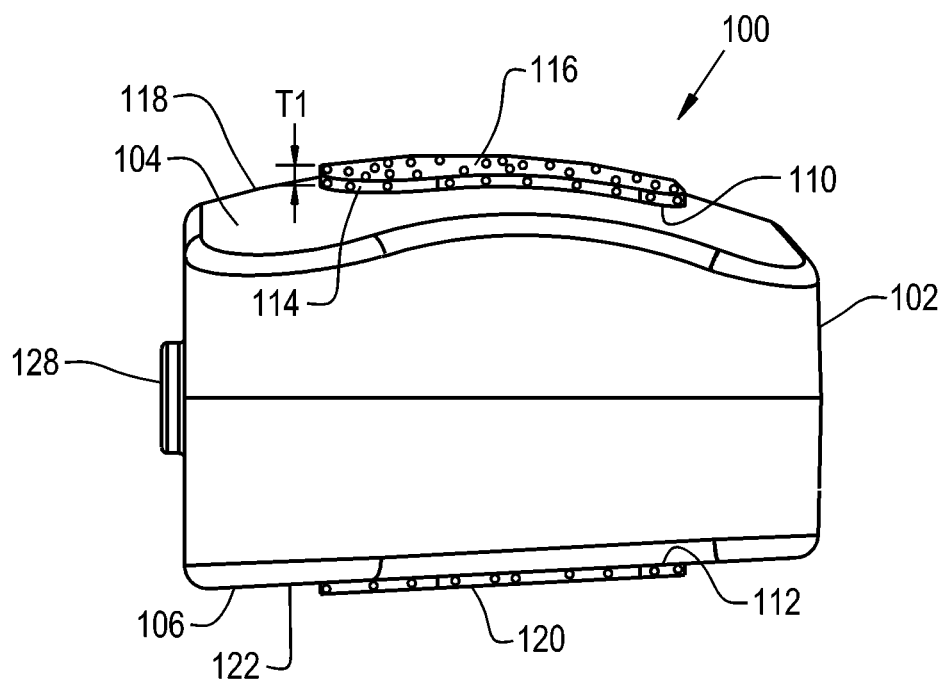
FIG. 28 is a side view of the orthopaedic implant shown in FIG. 27.
Figure 29:
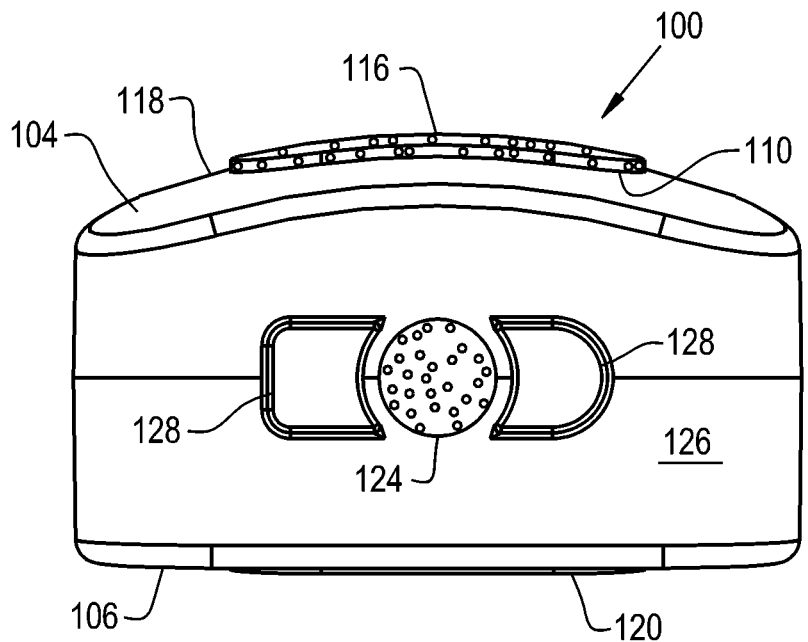
FIG. 29 is a front view of the orthopaedic implant shown in FIGS. 27-28.

Referring now to FIGS. 27-29, an embodiment of an orthopaedic implant 100 according to the present invention is shown that includes an implant body 102 formed from a substantially non-porous material having a first surface 104 and a second surface 106 opposite the first surface 104. As used herein, "substantially non-porous" indicates a porosity of 5% or less, so that the implant body 102 is mostly solid. The implant body 102 can be formed from a variety of different materials that are biocompatible and commonly used to form orthopaedic implants, including polyether ether ketone (PEEK), other polyaryl ether ketones (PAEKs), titanium, stainless steel, cobalt chrome, ultra-high molecular weight polyethylene (UHMWPE), or any previously described material. It should be appreciated that these materials are exemplary only and other biocompatible materials could be used to form the implant body. As shown in FIGS. 27-29, the implant body 102 is formed in the shape of a cervical cage for spinal applications, but other shapes can also be used, as shown further herein. The first surface 104 and second surface 106 can be curved, as shown, or can be formed as planar surfaces that are substantially flat. Alternatively, one of the surfaces 104, 106 can be formed as a surface with one or more curvatures while the other surface is planar.

A cavity 108 is formed in the implant body 102 extending through the first surface 104 and second surface 106 to form a continuous cavity 108 through the implant body 102. The cavity 108 has a first cavity entrance 110 formed through the first surface 104 and a second cavity entrance 112 (shown in FIG. 28) formed through the second surface 106. One or both of the cavity entrances 110, 112 can be concentrically formed through their respective surface 104, 106 so that the cavity entrances 110, 112 have a perimeter shape that approximately matches a perimeter shape of their respective surface 104, 106, with the cavity entrances 110, 112 having a smaller perimeter than their respective surfaces 104, 106. The cavity 108 can be formed to have a constant or varying shape throughout.

A load bearing member 114 comprising a substantially porous material having a first contact surface 116 is held within the cavity 108 that is formed within the implant body 102. As used herein, "substantially porous" indicates a porosity of at least 20%, but can be significantly higher. For example, the load bearing member 114 can have a total volume, that is the entire volume occupied by the load bearing member 114, of which 60% or more is defined by pores 117 formed in the load bearing member 114. In other words, 40% of the total volume of the load bearing member 114 can be occupied by structural material forming the load bearing member 114 while 60% of the total volume is occupied by empty spaced defined by the pores 117, in aggregate. If an extremely porous material is used to form the load bearing member 114, the pores 117, in aggregate, can occupy 80% or more of the total volume of the load bearing member 114. If desired, one or more therapeutic agents can be held within some or all of the pores 117 for elution into surrounding anatomic features after implantation of the orthopaedic implant 100 to increase the efficacy of the surgical procedure. A non-exhaustive list of possible therapeutic agents that can be provided in the pores 117 includes various growth factors, bone morphogenetic factors, bone morphogenetic proteins, anti-microbial agents, anti-inflammatories, anti-coagulants, painkillers, cytotoxic substances, stem cells, and any other substance, known or unknown, that is desirable to elute from the orthopaedic implant 100 following implantation. The material(s) used to form the load bearing member 114 should, like the implant body 102, be biocompatible so that the orthopaedic implant 100 is suitable for implantation at an anatomical site within a patient. It is also useful if the load bearing member 114 is formed from one or more materials that are non-resorbable, i.e., the material of the load bearing member 114 can maintain at least 90% of its original mass after being implanted in a living patient for at least a year. Examples of such materials are PEEK, tantalum, and titanium, but other porous materials are also contemplated as being used. The load bearing member 114 can comprise either a synthetic material, such as those previously described, or one or more naturally derived materials, such as a bone graft. The naturally derived material can also be, for example, cells or tissues harvested from the patient or a different organism, scaffolds created using collagen or other biomaterials, etc. It is useful, but not required, for the load bearing member 114 to substantially fill the cavity 108 so that at least 90% of the empty space in the implant body 102 defined by the cavity 108 is filled by the bearing member 114. Such filling of the cavity 108 by the load bearing member 114 makes it easier to hold the load bearing member 114 within the cavity 108 during implantation.

The first surface 104 defines a first peak 118, which is a point on the first surface 104 that has a maximum height, relative to a ground surface, when the second surface 106 of the implant body 102 is laid on the ground surface. The first peak 118 of implant body 102 is best shown in FIG. 28, where it can be seen that the first peak 118 is adjacent to the first cavity entrance 110. With further reference to FIG. 28, it can be seen that the first contact surface 116 of the load bearing member 114 extends out of the cavity 108 past the first cavity entrance 110 so that the first contact surface 116 extends past the first peak 118, i.e., the first contact surface 116 is proud of the first surface 104. In this sense, the first contact surface 116 defines a thickness T1 that extends past and projects from the first surface 104, which can be either constant or varying throughout the first contact surface 116. By extending the first contact surface 116 past the first peak 118 of the first surface 104, the first contact surface 116 can be placed in contact with an anatomic structure, such as a vertebrae, during implantation while isolating the first surface 104 from contact with the anatomic structure. Once implanted, the porous load bearing member 114 can then bear load from the anatomic structure while allowing for ingrowth of tissue into the load bearing member 114 through the pores 117.

Due to the varying shapes of anatomic structures and desired load bearing characteristics, the first contact surface 116 can be a curved surface or a planar surface. The relative sizing between the first surface 104 and the first contact surface 116 can also be adjusted, as desired, to balance the load bearing characteristics of the load bearing member 114. As can be seen, the first contact surface 116 defines a contact surface area and the first surface 104 defines a first surface area, with the contact surface area and first surface area together defining a top surface area of the orthopaedic implant 100. The relative percentage of the top surface area that the contact surface area makes up can be altered to give varying amount of contact surface for anatomic structures during implantation. It is contemplated that the contact surface area can be 40 to 90% of the total surface area when a large contact surface 116 is desired, or less than 40% of the total surface area when a smaller contact surface 116 is desired. It should be understood that the term "top surface area" is used for convenience of description only and not to limit the scope of the present invention.

Optionally, the load bearing member 114 can have a second contact surface 120 extending out of the cavity 108 past the second cavity entrance 112 so that it extends past a second peak 122 of the second surface 106 of the implant body 102. The second peak 122 of the second surface 106 is analogous to the first peak 118 of the first surface 104, with the key difference being that the second peak 122 defines a maximum height of the second surface 106 relative to a ground surface when the first surface 104 is laid on the ground surface. The second contact surface 120 can be configured and altered similarly to the first contact surface 116 so that the second contact surface 120 can be in contact with an anatomic structure following implantation. The second contact surface 120 can be a mirror image of the first contact surface 116 or a different configuration, depending on the desired load bearing characteristics of the load bearing member 114 caused by loads bearing on the first and second contact surfaces 116, 120 from surrounding anatomic structures. It can be useful if the pores 117 of the load bearing member 114 interconnect from the first contact surface 116 to the second contact surface 120 so that a travel path through the entirety of the load bearing member 114 can be formed through interconnected pores 117 formed therein.

To assist in implanting the orthopaedic implant 100, an opening 124 can be formed through another surface 126 of the implant body 102 to the cavity 108. The opening 124 can be any size or shape that allows for an insertion tool (not shown) to be placed within the opening 124 to help steady and position the orthopaedic implant 100 during implantation. The load bearing member 114 can partially extend into the opening 124, another material can be held in the opening 124, or the opening 124 can provide a clear path to the load bearing member 114 held in the cavity 108. In a similar manner, one or more protrusions 128 can be placed adjacent to the opening 124 that are shaped to interact with the insertion tool and provide a more stable connection between the orthopaedic implant 100 and the insertion tool. The opening 124 and protrusion(s) 128 can also be configured so that a removal tool (not shown), rather than an insertion tool, can interact with the opening 124 and protrusion(s) 128 to remove the orthopaedic implant 100 from a patient following implantation, if necessary.

Figure 30:
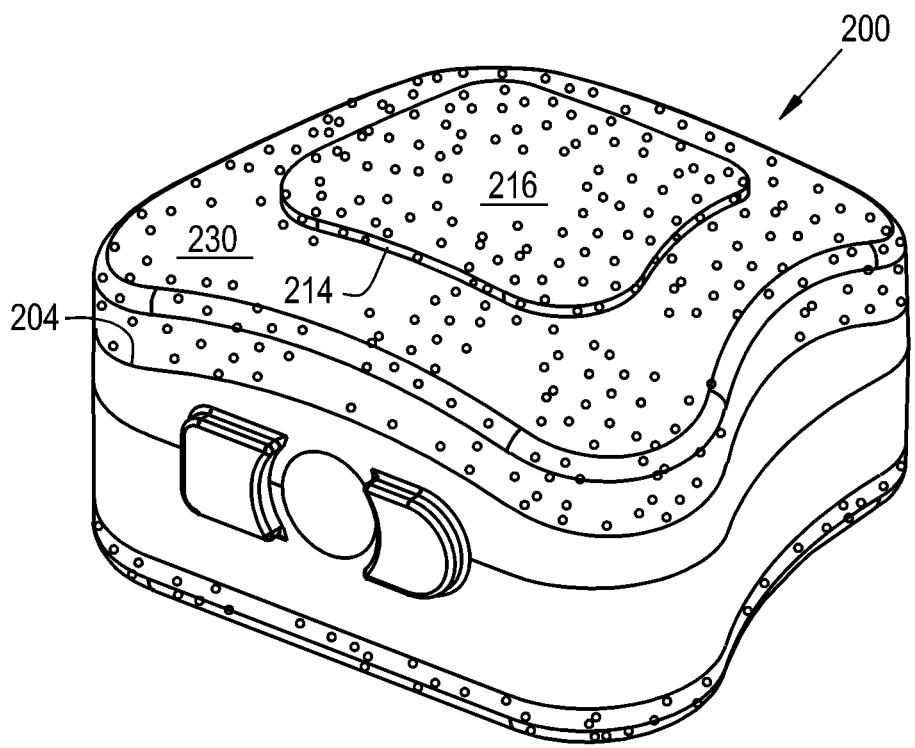
FIG. 30 is a perspective view of yet another embodiment of an orthopaedic implant according to the present invention.
Figure 31:
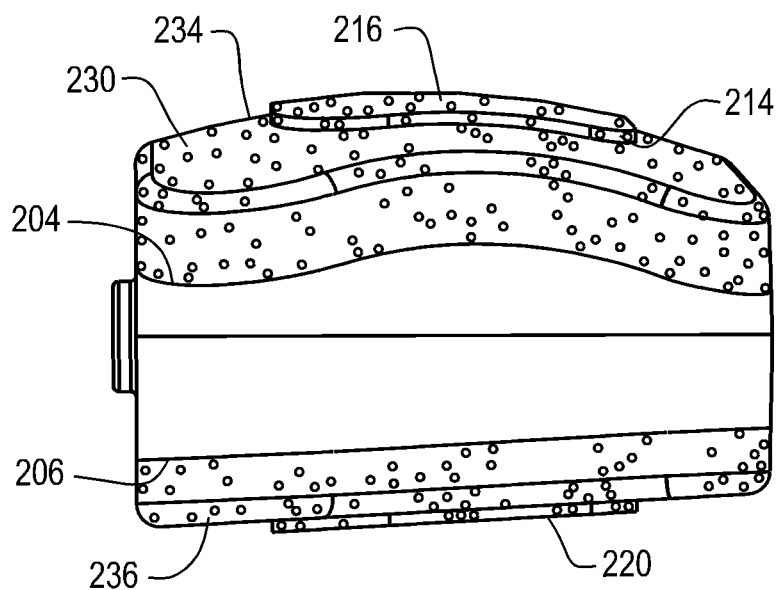
FIG. 31 is a side view of the orthopaedic implant shown in FIG. 30.

Referring now to FIGS. 30-31, another embodiment of an orthopaedic implant 200 is shown that is configured similarly to orthopaedic implant 100 previously described. For brevity of description, all features of orthopaedic implant 200 that are analogous to features of orthopaedic implant 100 are numbered similarly but raised by 100. As can be seen, the first surface 204 of the implant body 202 is covered by an ingrowth material 230, shown as a porous endplate. The ingrowth material 230 can cover all or part of the first surface 204 to encourage ingrowth of surrounding tissues into the ingrowth material 230 following implantation and provide good integration of the orthopaedic implant 200. The ingrowth material 230 can be formed of any material that encourages ingrowth of a desired body tissue into the ingrowth material 230. A non-exhaustive list of contemplated materials includes porous titanium, tantalum, hydroxyapatite, tricalcium phosphate, PEEK, PAEK, polymethyl methacrylate (PMMA), polylactic acid (PLA), and polyglycolic acid (PGA), but it should be understood that many other types of materials can be used as the ingrowth material 230. Since the load bearing member 214 will initially bear the brunt of the load from surrounding anatomic structures, the ingrowth material 230 can be formed of a lower strength material, with a higher porosity than the load bearing member 214, or both. For example, the load bearing member 214 can be formed of a reinforced PEEK material that has a porosity of 60% and the ingrowth material 230 can be formed of a PEEK material that has a porosity of 80%. This allows for orthopaedic implant 200 to have a higher strength material of the load bearing member 214 initially bear the brunt of the load from surrounding anatomic structures while a higher porosity material of the ingrowth material 230 allows for better tissue ingrowth to fixate the orthopaedic implant 200.

As shown in FIG. 31, the ingrowth material 230 has an ingrowth peak 234, which is the highest point of the ingrowth material 230 relative to a ground surface when the implant body 202 rests its second surface 206 on the ground surface. The first contact surface 216 of the load bearing member 214 extends out of the cavity 208 formed in the implant body 202 past the ingrowth peak 234, so that the first contact surface 216 can bear load from an anatomic structure following implantation and isolate the ingrowth material 230 from initially bearing load from the anatomic structure. The orthopaedic implant 200 can have a second ingrowth material 236 covering all or part of the second surface 206 of the implant body 202 and the load bearing member 214 can have a second contact surface 220 extending past the second ingrowth material 236 similarly to how the first ingrowth material 230 extends past the ingrowth peak 234 of the ingrowth material 230. In this sense, the ingrowth materials 230, 236 have surfaces that are analogous to the first and second surfaces 104, 106 of orthopaedic implant 100 and which the load bearing member 214 extends past.

Figure 32:
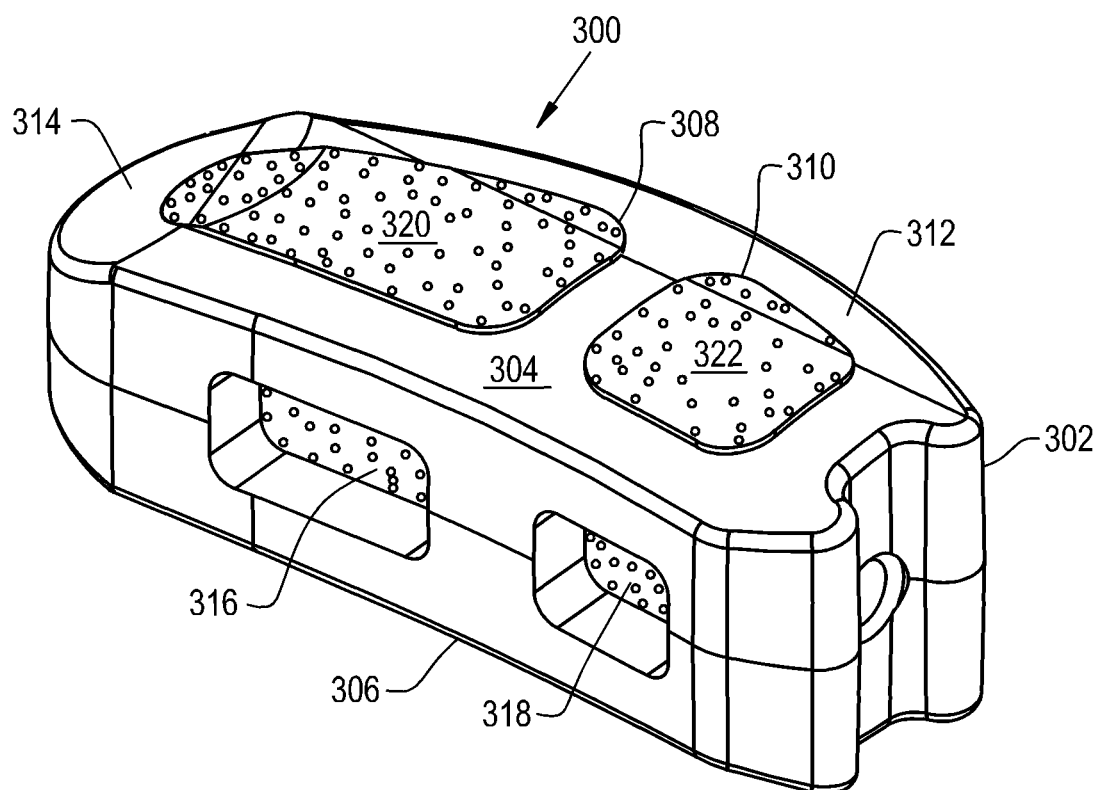
FIG. 32 is a perspective view of yet another embodiment of an orthopaedic implant according to the present invention.
Figure 33:
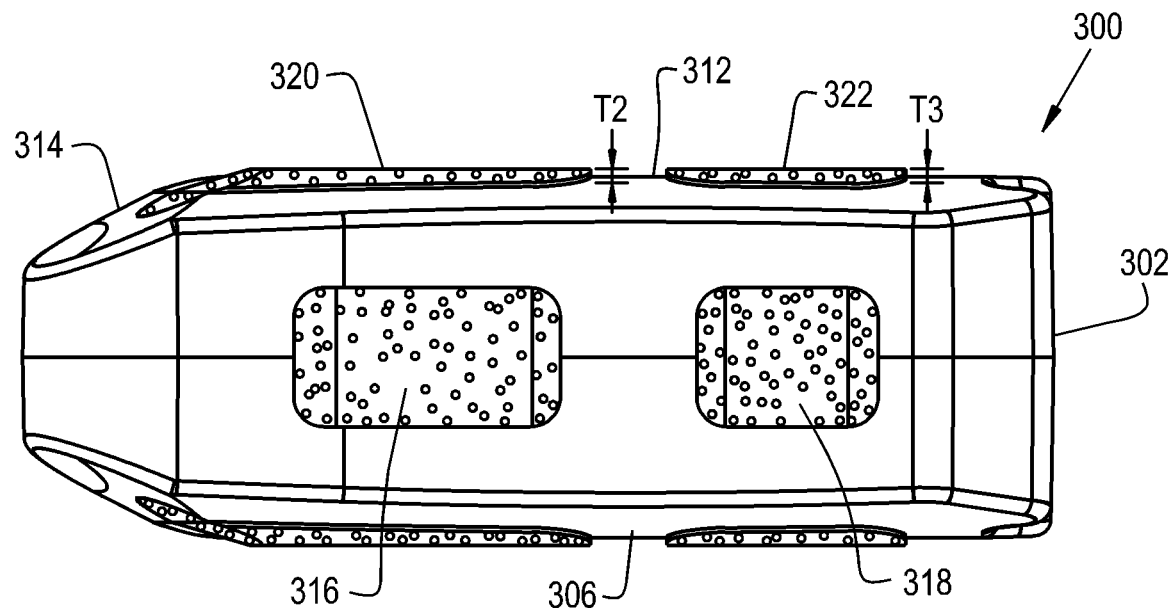
FIG. 33 is a front view of the orthopaedic implant shown in FIG. 32.
Figure 34:
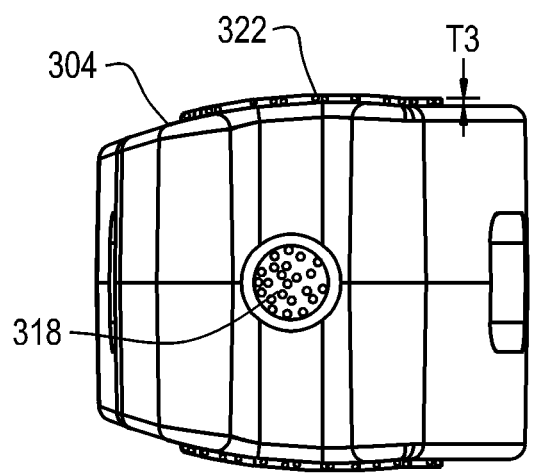
FIG. 34 is a side view of the orthopaedic implant shown in FIGS. 32-33.

Referring now to FIGS. 32-34, another embodiment of an orthopaedic implant 300 according to the present invention is shown that includes an implant body 302 configured to be used as a lumbar cage. The implant body 302 is comprised of a substantially non-porous material and has a first surface 304; a second surface 306 opposite the first surface 304; a first cavity 308 formed through the first surface 304 and second surface 306; and a second cavity 310 formed through the first surface 304 and second surface 306. As can be seen, the implant body 302 has a planar portion 312 that is flat and a curved portion 314 that has a sloped curvature. The cavities 308, 310 can be formed through the first and second surface 304, 306 all or partially within either the planar portion 312 or curved portion 314. A first load bearing member 316 is held within the first cavity 308 and a second load bearing member 318 is held within the second cavity 310. The first load bearing member 316 has a first contact surface 320 and the second load bearing member 318 has a third contact surface 322 that each extend out of their respective cavity 308, 310 past the plane of the planar portion 312, so that the contact surfaces 320, 322 can bear load from surrounding anatomic features following implantation. The load bearing members 316, 318 and their contact surfaces 320, 322 can be configured similarly to previously described load bearing members 114, 214, and even though the load bearing members 316, 318 are shown as having different sizes and total volumes, their size and total volume could be equal. The contact surfaces 320, 322 each define a respective thickness T2, T3 relative to the planar portion 312 of the first surface 304. The thicknesses T2, T3 of the contact surfaces 320, 322 can be equal to each other or could be different to provide different load bearing characteristics. For example, it may be desirable to provide load bearing member 316 with a thicker contact surface 320 than the contact surface 322 of load bearing member 318 due to the larger overall volume of load bearing member 316, in which case T2 would be greater than T3. It is also contemplated that the load bearing members 316 and 318 can be formed of different materials, have differing porosities, or be otherwise configured differently from one another to produce a desired healing effect.

Figure 35:
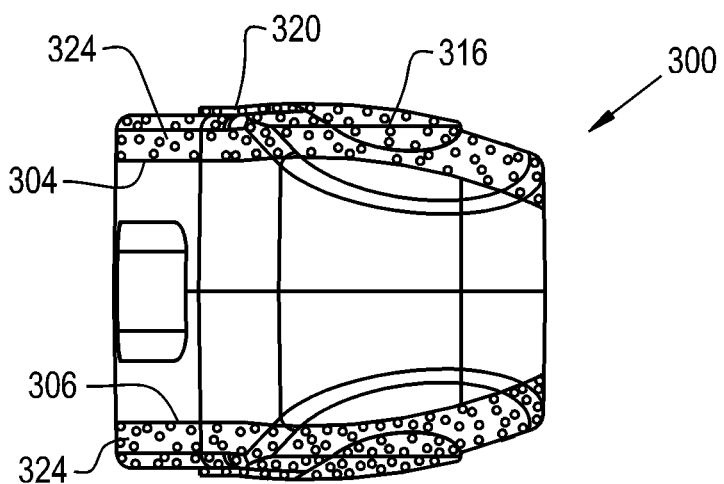
FIG. 35 is a side view of the orthopaedic implant shown in FIGS. 32-34 including an ingrowth material.

Referring now to FIG. 35, the orthopaedic implant 300 shown in FIGS. 32-34 is shown with ingrowth material 324 covering the first and second surfaces 304, 306 of the implant body 302. The ingrowth material 324 can be configured in an analogous manner to previously described ingrowth material 230.

Figure 36:
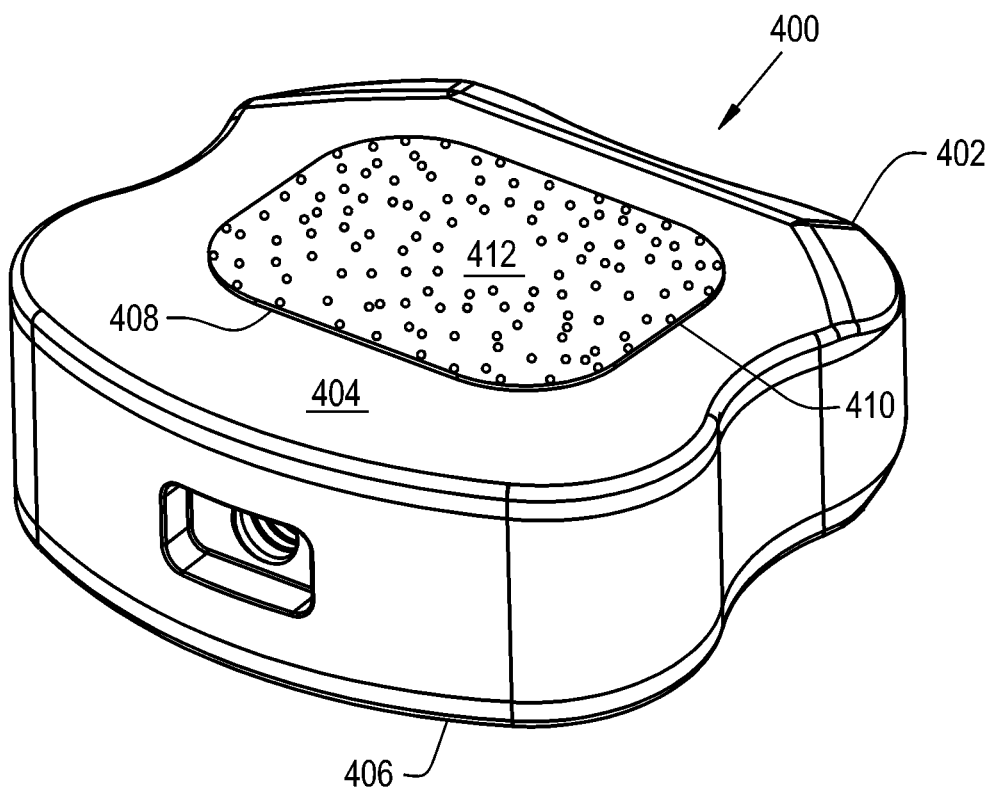
FIG. 36 is a perspective view of yet another embodiment of an orthopaedic implant according to the present invention.
Figure 37:
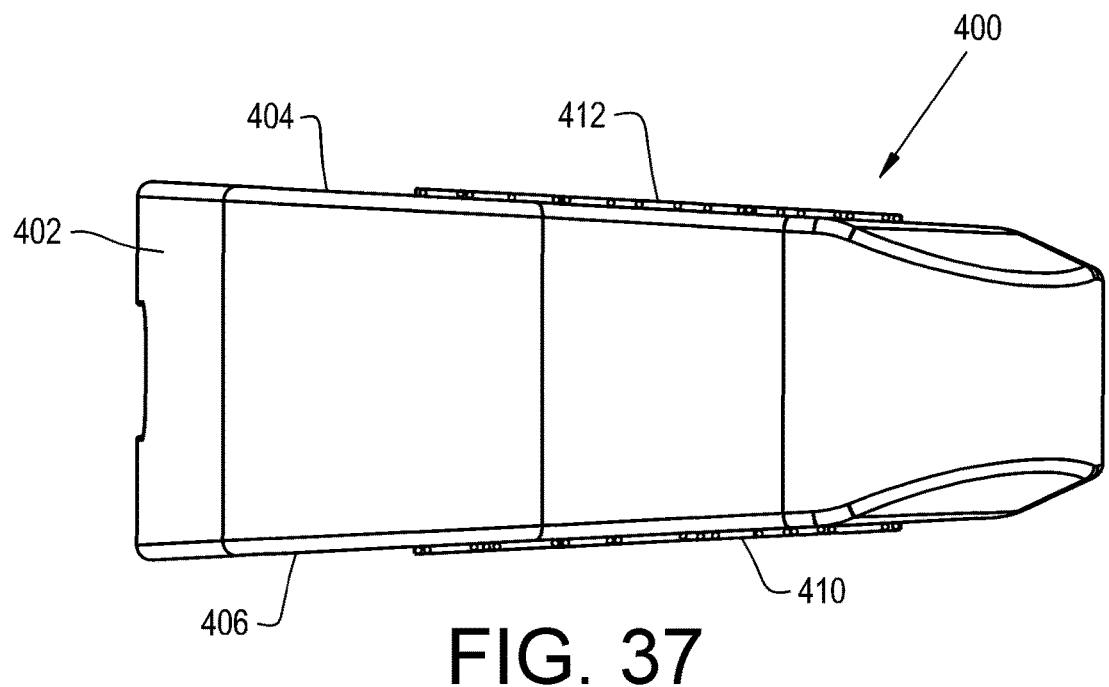
FIG. 37 is a side view of the orthopaedic implant shown in FIG. 36.

Referring now to FIGS. 36-37, another embodiment of an orthopaedic implant 400 according to the present invention is shown. The orthopaedic implant 400 includes an implant body 402, configured as an anterior lumbar interbody fusion cage, comprising a substantially non-porous material having a first surface 404, a second surface 406 opposite the first surface 404, and a cavity 408 that extends through the first surface 404 and second surface 406. As can be seen, the first surface 404 is a sloped planar surface that slopes downward from a front of the implant body 402 toward a back of the implant body 402. It should be appreciated that the slope of the first surface 404 can be adjusted, as desired, to provide a variety of shapes for the implant body 402 that are suitable for different surgical procedures.

A load bearing member 410 comprising a substantially porous material is held within the cavity 408. The load bearing member 410 has a first contact surface 412 that extends out of the cavity 408 and is proud of a portion of the first surface 404 to which the first contact surface 412 is immediately adjacent. Put another way, the first contact surface 412 outwardly projects from the cavity 408 so that it will contact surrounding anatomic features when the orthopaedic implant 400 is implanted and isolate portions of the first surface 404 immediately adjacent to the cavity 408 from initially bearing load from the surrounding anatomic features. Since the first surface 404 is sloped, the first contact surface 412 does not necessarily extend past a peak of the first surface 404, as previously described first contact surfaces do. However, in all other aspects, load bearing member 410 and first contact surface 412 can be configured similarly to previously described load bearing members and contact surfaces.

Figure 38:
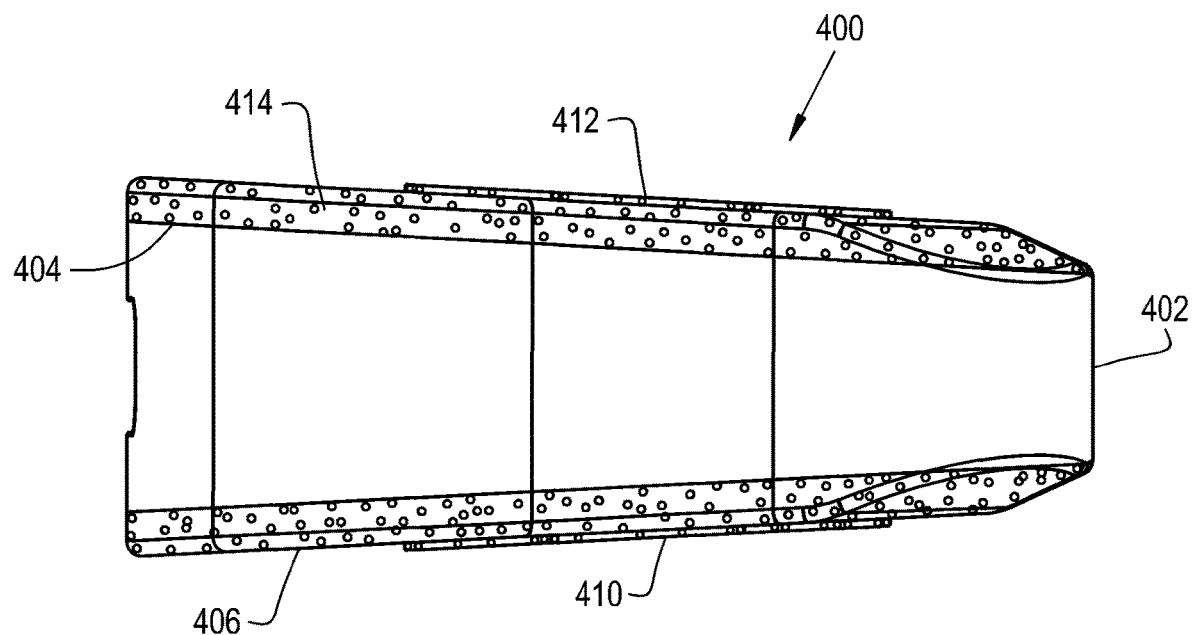
FIG. 38 is a side view of the orthopaedic implant shown in FIGS. 36-37 including an ingrowth material.

Referring now to FIG. 38, the orthopaedic implant 400 shown in FIGS. 36-37 is shown with an ingrowth material 414 covering the first surface 404 of the implant body 402. The ingrowth material 414 can be configured similarly to previously described ingrowth materials. As can be seen, the load bearing member 410 is proud of a portion of the ingrowth material 414 similarly to how the load bearing member 410 shown in FIGS. 36-37 is proud of a portion of the first surface 404.

Figure 39:
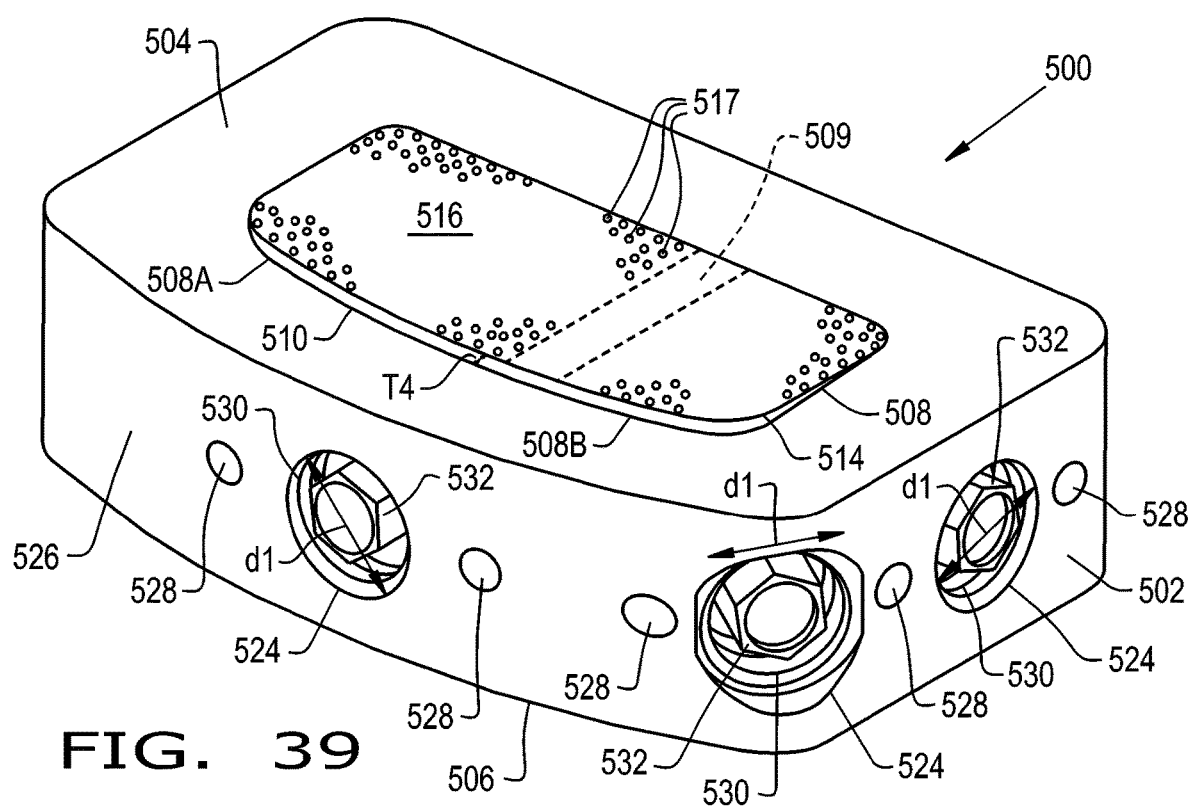
FIG. 39 is a perspective view of an orthopaedic implant according to the present invention.

Referring now to FIG. 39, another embodiment of an orthopaedic implant 500 according to the present invention is shown. The orthopaedic implant 500 includes an implant body 502 formed from a substantially non-porous material having a first surface 504 and a second surface 506 opposite the first surface 504. The first surface 504 and second surface 506 can be curved, as shown, or can be formed as planar surfaces that are substantially flat. Alternatively, one of the surfaces 504, 506 can be formed as a surface with one or more curvatures while the other surface is planar.

A cavity 508 is formed in the implant body 502 extending through the first surface 504 and second surface 506 to form a continuous cavity 508 through the implant body 502. The cavity 508 has a first cavity entrance 510 formed through the first surface 504 and a second cavity entrance 512 (FIG. 40) formed through the second surface 506. One or both of the cavity entrances 510, 512 can be concentrically formed through their respective surface 504, 506 so that the cavity entrances 510, 512 have a perimeter shape that approximately matches a perimeter shape of their respective surface 504, 506, with the cavity entrances 510, 512 having a smaller perimeter than their respective surfaces 504, 506. The cavity 508 can be formed to have a constant or varying shape throughout.

A load bearing member 514 comprising a substantially porous material having a first contact surface 516 and having pores 517 is held within the cavity 508 that is formed within the implant body 502. The load bearing member 514 and its contact surface 516 can be configured similarly to previously described load bearing members 114, 214 and 410 and their respective contact surfaces 116, 216, and 412.

Preferably, and as illustrated, the first contact surface 516 of the load bearing member 514 extends out of the cavity 508 past the first cavity entrance 510 so that the first contact surface 516 extends past the first surface 504. In this sense, the first contact surface 516 defines a thickness T4 that extends past and projects from the first surface 504, which can be either constant or varying throughout the first contact surface 516. However, in another embodiment, the thickness T4 has a constant value of zero, thus the first contact surface 516 is flush with the first surface 504. By extending the first contact surface 516 past the first surface 504, the first contact surface 516 can be placed in contact with an anatomic structure, such as a vertebra, during implantation while isolating the first surface 504 from contact with the anatomic structure. Once implanted, the porous load bearing member 514 can then bear load from the anatomic structure while allowing for ingrowth of tissue into the load bearing member 514 through the pores 517.

One or more first openings 524 can be formed through another surface 526 of the implant body 502 to the cavity 508. The load bearing member 514 can partially extend into the first openings 524, another material can be held in the first openings 524, or the first openings 524 can provide a clear path to the load bearing member 514 held in the cavity 508. The first openings 524 can be any size or shape that allows for an insertion/delivery tool, to be described more fully below, to be placed within a first opening 524 (e.g., coupled to the first opening 524) for delivery of a material agent to the load bearing member 514 via the first opening 524 during a surgical procedure for implanting the orthopaedic implant 500. Preferably, the first openings 524 are circular openings having a threaded outer portion 530 with a diameter $d_1$, however the scope of the present invention covers first openings 524 having one or more different diameters or different geometric shapes with associated geometric parameters (e.g., parameters describing ellipses, squares, rectangles), and may have outer portions 530 that are not threaded.

Additionally, one or more second openings 528 can be placed adjacent to the first openings 524, shaped to interact with the insertion/delivery tool (described below) for providing a more stable connection between the orthopaedic implant 500 and the insertion/delivery tool for delivery of the material agent to the load bearing member 514 via the first opening 524 and/or for positioning the orthopaedic implant 500 during implantation. The first openings 524 and the second openings 528 can also be configured so that the insertion/delivery tool can interact with the first opening 524 and the second openings 528 to charge the load bearing member 514 with a material agent (described more fully below), or to recharge the load bearing member 514 during a second surgical procedure, if necessary.

The orthopaedic implant 500 includes plugs 532 that are coupled to the first openings 524. The plugs 532 prevent the material agent of the load bearing member 514, particularly after the load bearing member 514 has been charged with the material agent from the insertion/delivery tool via the first openings 524, from flowing out of the load bearing member 514 via the first openings 524 once the insertion/delivery tool has finished charging the load bearing member 514 and/or has been de-coupled from the first openings 524.

In another embodiment, the cavity 508 may optionally be divided into two or more sub-cavities. By way of an exemplary embodiment, the cavity 508 may optionally be divided into two sub-cavities 508A and 508B by a divider 509, formed from the same substantially non-porous material of the implant body 502. The load bearing member 514 may include porous material of different porosities held within the two sub-cavities 508A and 508B. In one embodiment, one or more first openings 524 are formed through the third surface 526 to each of the sub-cavities 508A and 508B.

Figure 40:
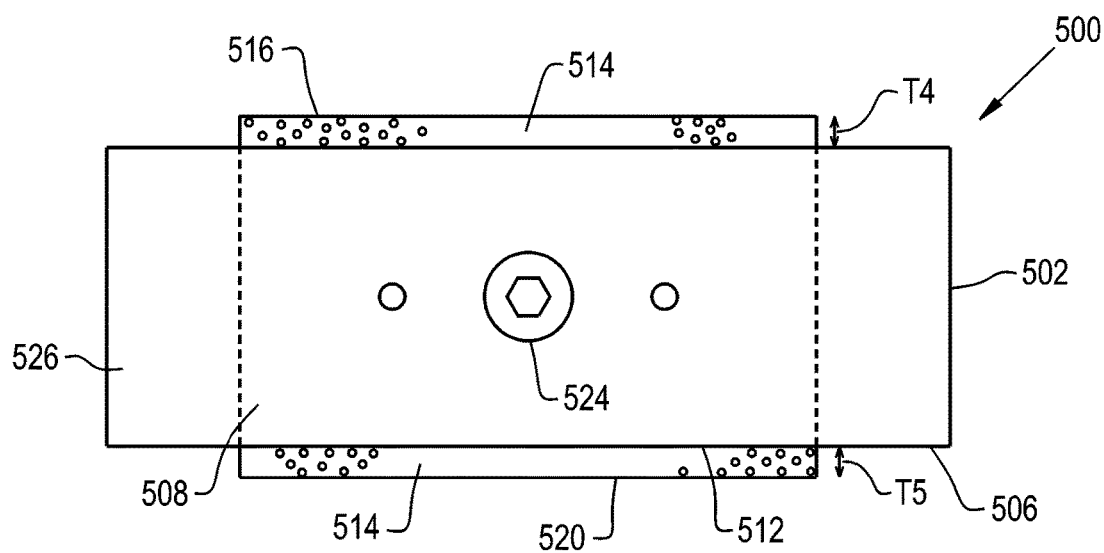
FIG. 40 is a side view of the orthopaedic implant of FIG. 39, according to an embodiment of the present invention.

FIG. 40 illustrates another view of the orthopaedic implant 500, according to an embodiment of the present invention. Optionally, the load bearing member 514 can have a second contact surface 520 extending out of the cavity 508 past the second cavity entrance 512 so that it extends past the second surface 506 of the implant body 502. The second contact surface 520 can be configured and altered similarly to the first contact surface 516 so that the second contact surface 520 can be in contact with an anatomic structure following implantation. The second contact surface 520 can be a mirror image of the first contact surface 516 or a different configuration, depending on the desired load bearing characteristics of the load bearing member 514 caused by loads bearing on the first and second contact surfaces 516, 520 from surrounding anatomic structures. It can be useful if the pores 517 of the load bearing member 514 interconnect from the first contact surface 516 to the second contact surface 520 so that a travel path through the entirety of the load bearing member 514 can be formed through interconnected pores 517 formed therein.

As illustrated, the second contact surface 520 defines a thickness T5 that extends past and projects from the second surface 506, which can be either constant or varying throughout the second contact surface 506. However, in another embodiment, the thickness T5 has a constant value of zero, thus the second contact surface 520 is flush with the second surface 506.

Figure 41:
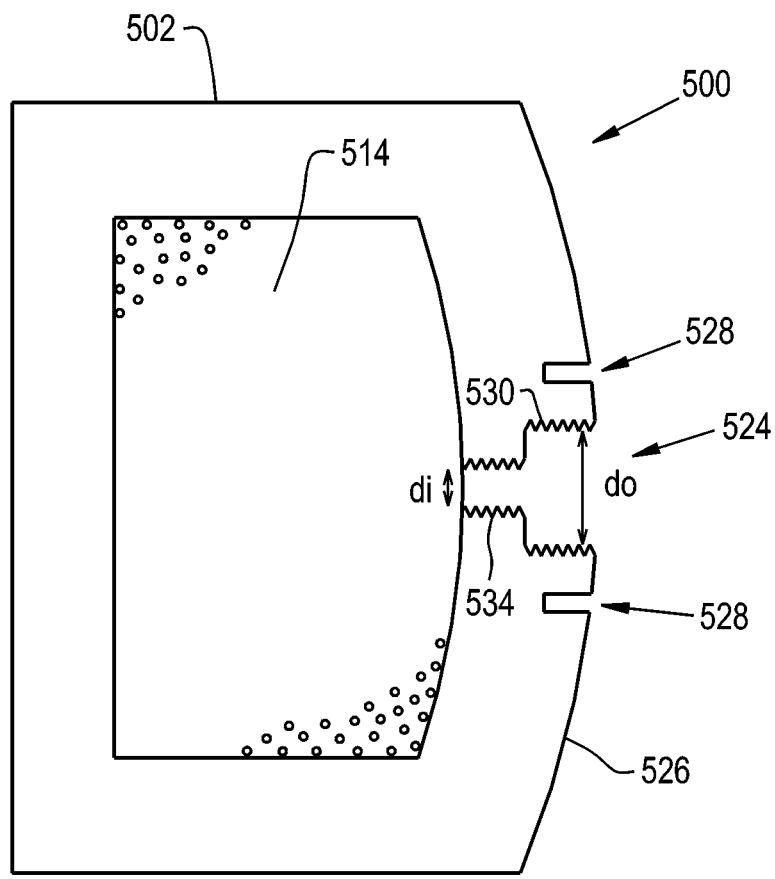
FIG. 41 is a cross-sectional view of the orthopaedic implant of FIG. 39, with the plug removed, according to an embodiment of the present invention.

FIG. 41 illustrates a cross-sectional view of the orthopaedic implant 500, with the plug 532 removed, according to an embodiment of the present invention. For ease of illustration, only one first opening 524 is shown. The first opening 524 includes the threaded outer portion 530 and an inner portion 534, which is preferably threaded, however the scope of the invention covers the inner portion 534 being non-threaded, and having instead notches replacing the threads, or other means of removably-coupling a plug (shown in FIG. 42). The threaded outer portion 530 has an outer diameter $d_o$ and the threaded inner portion 534 has an inner diameter $d_1$. In one embodiment, the inner diameter $d_i$ is less than the outer diameter $d_o$. Reference numbers that are the same as the reference numbers of the previous figures refer to the same features.

Figure 42:
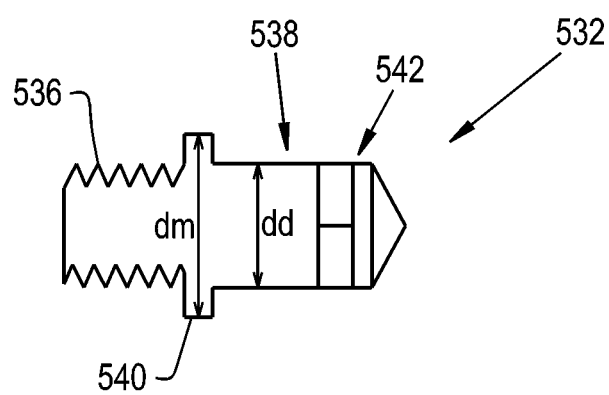
FIG. 42 is a top view of the plug of the orthopaedic implant of FIG. 39, according to an embodiment of the present invention.

FIG. 42 illustrates the plug 532, according to an embodiment of the present invention. The plug 532 includes a threaded proximal portion 536, a distal portion 538, and a middle portion 540 positioned between the threaded proximal portion 536 and the distal portion 538. The threaded proximal portion 536 is configured to be coupled (e.g., threaded) with the threaded inner portion 534 of the first opening 524. However, the scope of the present invention covers other means of removably-coupling a proximal portion 536 of the plug 532, in which the proximal portion 536 has, for example, ridges for removably-coupling with, for example, notches of the inner portion 534. The middle portion 540 has a diameter $d_m$ and the distal portion 538 has a diameter $d_d$. The distal portion 538 has a distal end 542, preferably shaped for receiving a rotating means, such as a socket (not shown), for example. Although in the embodiment as illustrated, the distal end 542 is shaped as a hexagon, the scope of the present invention covers the distal end 542 formed in any shape (e.g., shaped as a cylinder containing a socket for receiving a corresponding rotating means). In one embodiment, the diameter $d_m$ of the middle portion 540 is less than or equal to the diameter $d_o$ of the threaded outer portion 530 of the first opening 524 and greater than the diameter $d_i$ of the threaded inner portion 534 of the first opening 524, and the diameter $d_d$ of the distal portion 538 is less than the diameter $d_o$ of the threaded outer portion 530 of the first opening 524 for accommodating a rotating means within the threaded outer portion 530 of the first opening 524 for threading the plug 532 into the inner portion 534 of the first opening 524 and de-threading (i.e., removing or decoupling) the plug 532 from the inner portion 534 of the first opening 524.

Figure 43:
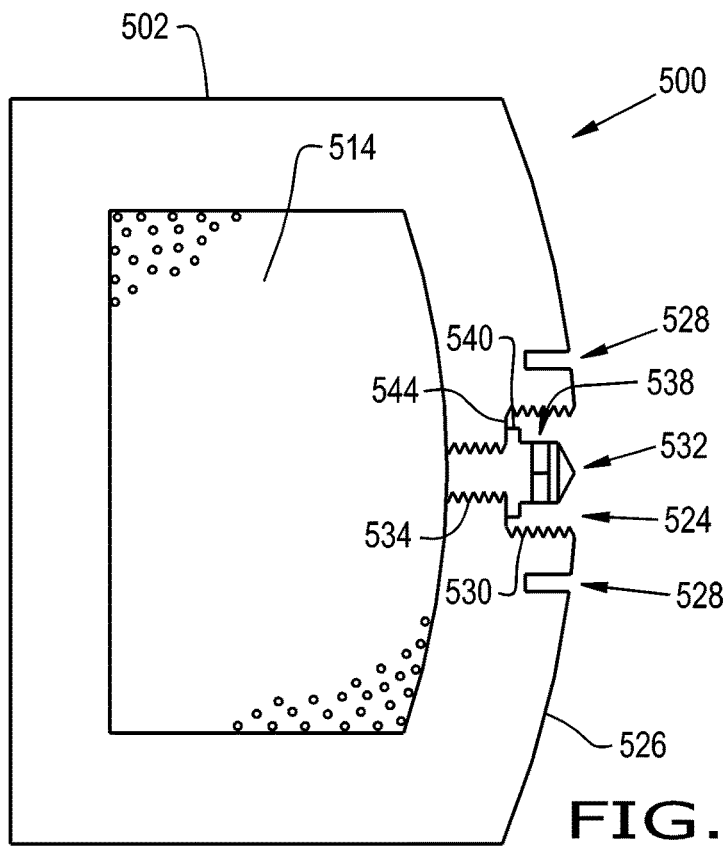
FIG. 43 is a cross-sectional view of the orthopaedic implant of FIG. 39, including the plug 532, coupled to the first opening for sealing the first opening, according to an embodiment of the present invention.

FIG. 43 illustrates a cross-sectional view of the orthopaedic implant 500, including the plug 532 coupled to the first opening 524 for sealing the first opening 524, according to an embodiment of the present invention. For ease of illustration, only one first opening 524 is shown. As illustrated, the diameters $d_m$ and $d_d$ (shown in FIG. 42) of the middle and distal portions 540, 538, respectively, of the plug 532, are less than the diameter $d_o$ (shown in FIG. 41) of the threaded outer portion 530 of the first opening 524. In one embodiment, once the plug 532 is coupled in place within the first opening 524, via application of a rotating means (not shown), the middle portion 540 of the plug 532 may abut against a wall 544 separating the threaded outer portion 530 of the first opening 524 from the threaded inner portion 534 of the first opening 524. Although the coupling of the threaded proximal portion 536 with the threaded inner portion 534 of the first opening 524 may adequately seal the first opening 524 of the implant 500 from leaking a material agent contained within the load bearing member 514, the abutment of the middle portion 540 of the plug 532 against the wall 544 may assist in sealing the first opening 524, as well as preventing the plug 532 from being threaded too far into the first opening 524. In addition, as seen further below in conjunction with FIG. 44, the middle portion 540 may provide a means for a plunger 606 of an insertion/delivery tool 600 to slide the plug 532 in a cannula 604 of the insertion/delivery tool to position the plug 532 adjacent to the threaded inner portion 534, such that the plug 532 may subsequently be coupled to the threaded inner portion 534 via a rotating means, as described more fully further below.

Figure 44:
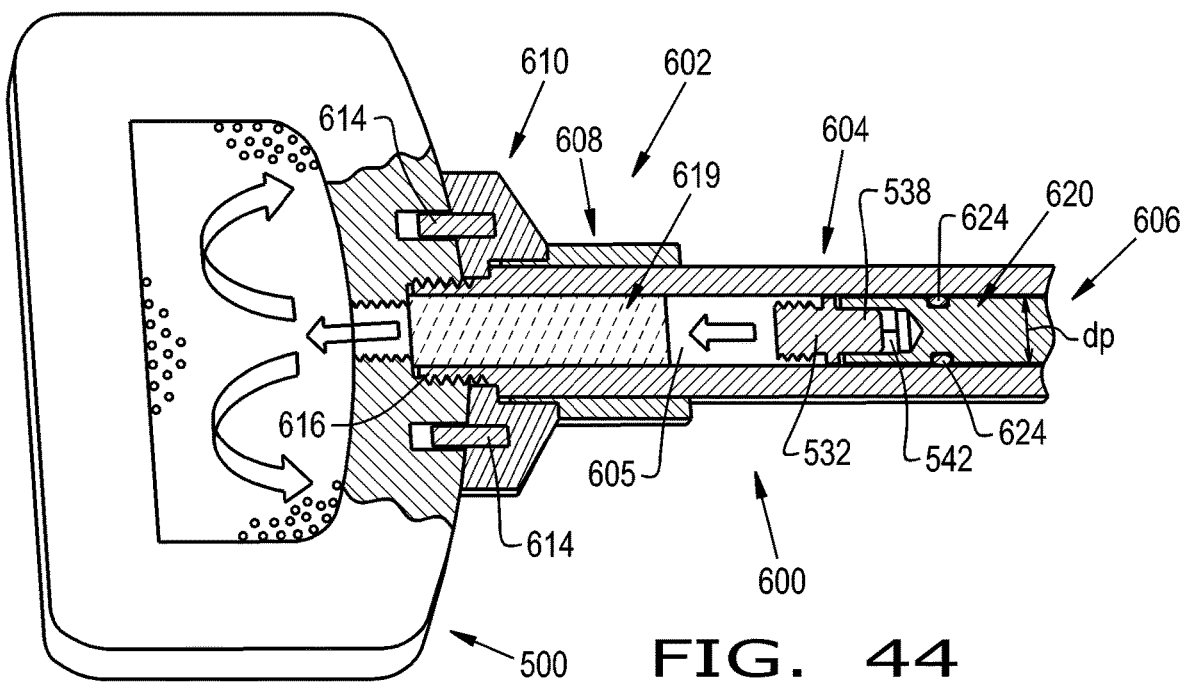
FIG. 44 illustrates a cross-sectional view of an insertion/delivery (ID) tool coupled to the orthopaedic implant of FIG. 39, according to an embodiment of the present invention.
Figure 45:
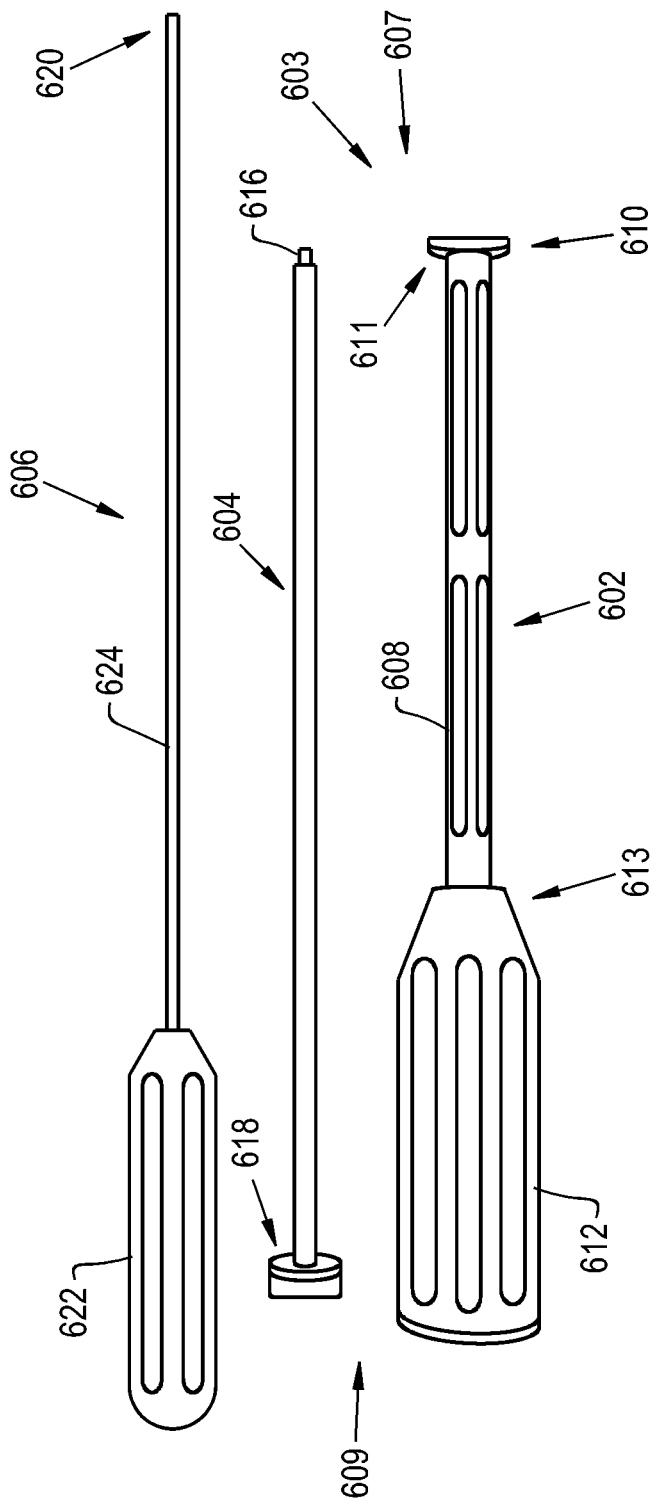
FIG. 45 is a perspective view of the components of the ID tool of FIG. 44, according to an embodiment of the present invention.

FIG. 44 illustrates a cross-sectional view of the insertion/delivery (ID) tool 600 coupled to the orthopaedic implant 500 illustrated in FIGS. 39-41 and FIG. 43, according to an embodiment of the present invention. The insertion delivery tool 600 is shown coupled to the orthopaedic implant 500 for ease of description. FIG. 45 illustrates several components of the ID tool 600, when the ID tool 600 is decoupled from the orthopaedic implant 500, according to an embodiment of the present invention. Reference is made to both FIGS. 44 and 45 in the following description.

The ID tool 600 includes an inserter 602, a cannula 604 (i.e., a tube), and a plunger 606. In one embodiment, the inserter 602 includes a tubular portion 608, an attachment portion 610 positioned at a first end 611 of the tubular portion 608, and a handle portion 612 positioned around a second end 613 of the tubular portion 608. The attachment portion 610 may include one or more pins 614 configured to engage with (also referred to as couple with or interact with) the one or more second openings 528 for enabling the inserter 602 to insert and/or position the orthopaedic implant 500 during implant, and/or stabilize the orthopaedic implant 500 for delivery of a material agent 619 to the orthopaedic implant 500 via the first openings 524, as will be described shortly. In addition, the attachment portion 610, including the one or more pins 614 engaged with the one or more second openings 528, in combination with the tubular portion 608, provides a means for guiding the cannula 604 to the first opening 524 and stabilizing the orthopaedic implant 500 when the cannula 604 is for coupled to the first opening 524.

The cannula 604 includes a tubular passage 605 having an attachment portion 616 configured to be coupled to the orthopaedic implant 500. In one embodiment, the attachment portion 616 is threaded. The threaded attachment portion 616 is configured to thread with the outer threaded portion 530 of the first opening 524. However, the scope of the invention covers the attachment portion 616 being non-threaded, having instead other means of attachment for attaching to the outer portion 530 of the first opening 524. The cannula 604 also includes a receiving end 618 configured to receive the material agent 619 and the plug 532 coupled to a the plunger 606. The receiving end 618 may also be configured to receive a rotatable means (not shown) for rotating the cannula 604 for threading the threaded attachment end 616 with the threaded outer portion 530 of the first opening 524 for securely, but removably, coupling the cannula 604 to the orthopaedic implant body 500 (e.g., to the first opening 524). As illustrated, the inserter 602 and the cannula 604 are configured such that the cannula 604 may be positioned in the tubular portion 608 of the inserter 602 (i.e., slid inside the tubular portion 608 of the inserter 602) for coupling the cannula 604 to the orthopaedic implant 500 via the threaded outer portion 530 of the first opening 524.

The insertion/delivery tool 600 also comprises the plunger 606. The plunger 606 includes a first end 620 and a handle end 622, connected to each other via a rod 624. The first end 620 is configured to couple with the distal portion 538 of the plug 532 for pushing the plug 532, and the material agent 619 residing in the cannula 604 between the plug 532 and the attachment end 616, through the cannula 604 towards the first opening 524. In one embodiment, the first end 620 is a hexagon-shaped socket configured to couple with a hexagon-shaped distal end 542 of the plug 532. Once the first end 620 of the plunger 606 is coupled with the distal end 542 of the plug 532, a force may be applied to the handle end 622 for pushing the plug 532 (and any material agent 619 residing in the cannula 604 between the plug 532 and the attachment end 616) through the cannula 604, thereby forcing the material agent 619 into the load bearing member 514 via the first opening 524, and once the threaded proximal portion 536 of the plug 532 is pushed up against the threaded inner portion 534 of the first opening 524, the handle end 622 may be rotated for threading the plug 532 into the threaded inner portion 534 of the first opening 524, thereby sealing the first opening 524 against expulsion or leakage of the material agent 619 from the load bearing member 514. In one embodiment, the plunger 606 comprises one or more sealing rings 624, such as O-rings, positioned around the rod 624 for preventing leakage of the material agent 619 into a portion of the cannula 604 between the sealing ring 624 and the receiving end 618 of the cannula 604 as the plunger 606 is being pushed down the cannula 604 in the direction of the first opening 524.

In one embodiment, and as illustrated, the tubular passage 605 has a tubular passage diameter $d_p$, and the middle diameter $d_m$ of the plug 532 is equal to the tubular passage diameter $d_p$ and the distal diameter da of the plug 532 is less than the tubular passage diameter $d_p$.

In another embodiment, the inserter 602 and the cannula 604 positioned within the tubular portion 608 of the inserter 602 may collectively be referred to as a tubular assembly 603 having the tubular passage 605. The tubular assembly also includes a first end 607 configured to couple (i.e., attach) to the orthopaedic implant 500 and a second end 609 configured to receive the material agent 619, the plug 532 and the plunger 606.

Figure 46:
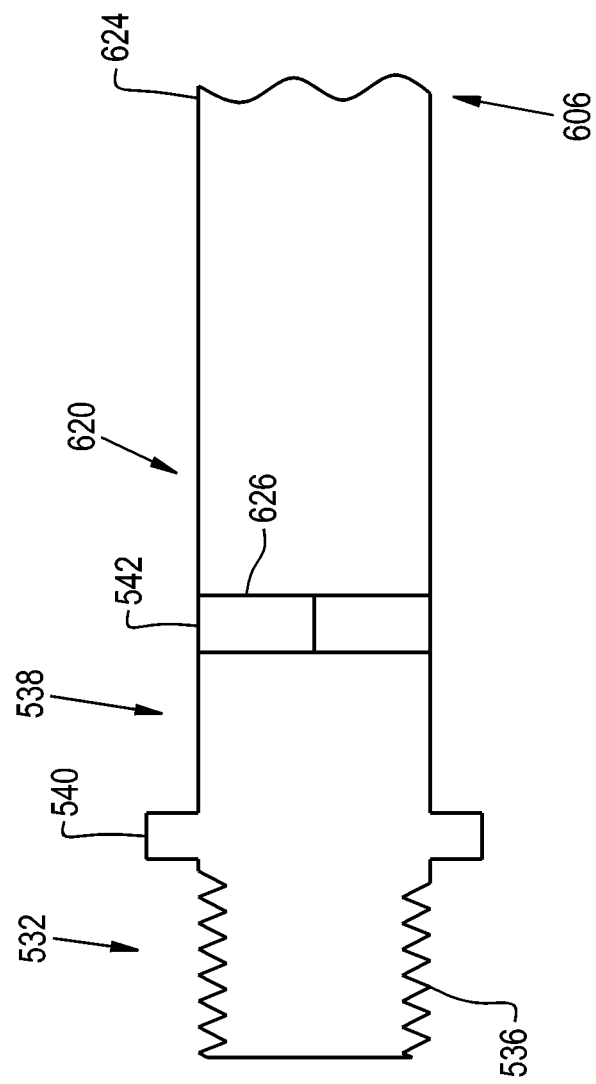
FIG. 46 is a top view of the first end of the plunger of the ID tool, according to one embodiment of the present invention.

FIG. 46 illustrates the first end 620 of the plunger 606, according to another embodiment of the present invention. In this embodiment, the first end 620 is connected to the distal end 542 of the plug 532 at a joint 626, or in other words, the first end 620 includes the plug 532. In operation, once the inserter 602 and the cannula 604 have been coupled to the orthopaedic implant 500, and the material agent is placed in the receiving end 618 of the cannula 604, and the plunger 606, including the first end 620 connected to the plug 532, has pushed the threaded proximal portion 536 up against the threaded inner portion 534 of the first opening 524, the plunger 606 is rotated, causing the plug to be threaded into the threaded inner portion 534. In one embodiment, the first end 620 is connected to the distal end 542 of the plug 532 in such a manner that once the threading of the plug is complete, thereby sealing the first opening 524, any further rotation of the plunger 606 causes the first end 620 to break with the distal end 542 of the plug 532 along the joint 626, allowing removal of the plunger 606 from the cannula 604. In one embodiment, the distal end 542 is configured as a hexagon, or any other shape, to allow the plug 532 to be de-threaded (i.e., removed) from the first opening 524 at a later time. In another embodiment, the distal end 542 is not configured to accommodate any rotational means for removing the plug 532, and thus the plug 532 is permanently coupled to the first opening 524.

Figure 47:
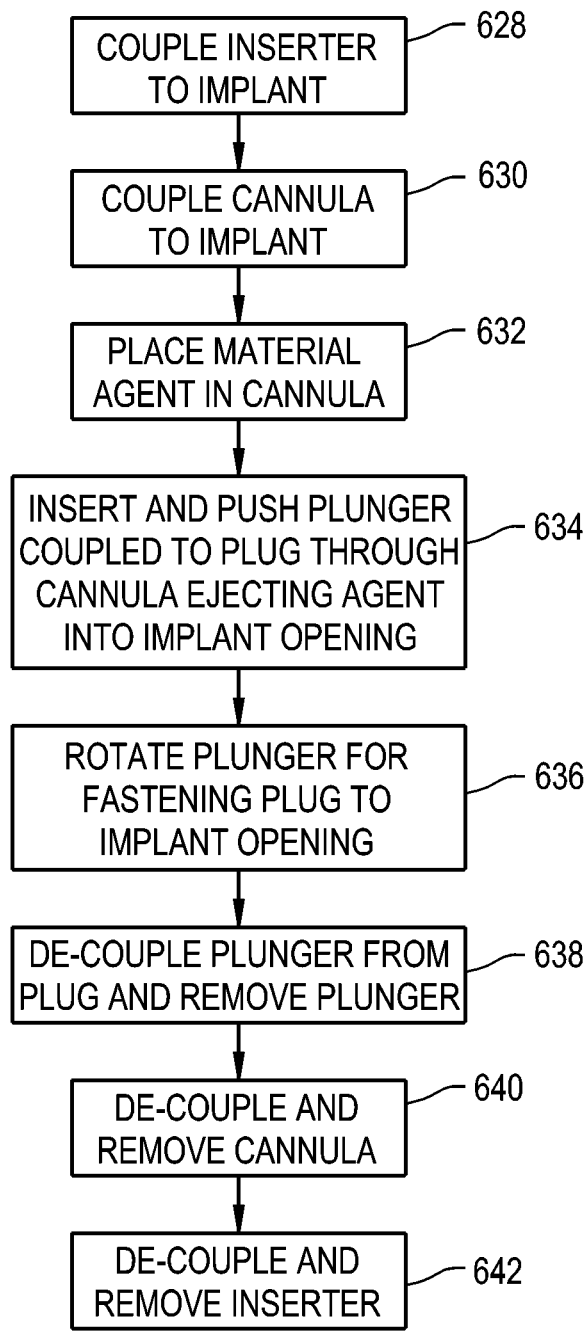
FIG. 47 are method steps for charging of the orthopaedic implant of FIG. 39 with a material agent.

FIG. 47 shows method steps for charging of the orthopaedic implant 500 with the material agent 619.

In step 628, the inserter 602 is coupled to the orthopaedic implant 500. In one embodiment, the one or more pins 614 of the attachment portion 610 of the inserter 602 is coupled to the one or more second openings 528 of the orthopaedic implant 500. In one embodiment, the two second openings 528 are formed in the surface 526, also referred to as a side surface of the orthopaedic implant. The surface 526 is formed between the first surface 504 and the second surface 506 of the orthopaedic implant 500. In an embodiment, the two second openings are formed to straddle the first opening 524 in the surface 526.

In step 630, the cannula 604 is coupled to the orthopaedic implant 500. In one embodiment, the attachment portion 616 of the cannula 604 is slid into the inserter 602 until the attachment portion 616 reaches the outer portion 530 of the first opening 524. The cannula 604 is then rotated, preferably via use of a rotating means, such as a socket, wrench, etc., applied to the receiving end 618 of the cannula 604, causing the attachment portion 616 to rotate, thereby coupling the attachment portion 616 to the outer portion 530 of the first opening 524. In one embodiment, the both the attachment portion 616 and the outer portion 530 are threaded, and the rotation of the cannula 604 causes the threaded attachment portion 616 to thread with the threaded outer portion 530, thereby coupling the cannula 604 to the orthopaedic implant 500, or according to one embodiment, to the first opening 524 of the orthopaedic implant 500.

In step 632, the material agent 619 is placed into the cannula 604 via the receiving end 618. In one embodiment, the material agent is a flowable material. The scope of the present invention covers flowable materials, such as bone pastes, bone putties, bone grafts, or therapeutics, for example, antibiotics, blood plasmas, bone marrow, pain medications, or drugs, such as tumor-fighting drugs, all having conventional viscosities known to those of skill in the art. Furthermore, the scope of the present invention covers any biological material agents that may be embodied as a flowable material. In addition, the scope of the present invention covers material agents having a range of viscosities, which in combination with a porous load bearing member 514 having various interconnectivities and pore sizes, are deliverable into the porous load bearing member 514 via the first opening 524, the cannula 604 and the plunger 606.

In step 634, the first end 620 of the plunger 606 coupled to the plug 532 is inserted into and pushed through the cannula 604 in the direction of the first opening 524, thereby enabling the plug 532 to push the material agent 619 in the direction of the first opening 524 and forcing the material agent 619 through the first opening 524 for charging the porous load bearing member 514 of the orthopaedic implant 500 with the material agent 619. In one embodiment, the first end 620 of the plunger 606 is removeably-coupled to the distal end 542 of the plug 532, via for example, a socket. In another embodiment, the first end 620 of the plunger 606 is breakably-coupled to the distal end 542 of the plug 532 at a joint 626 between the distal portion 542 and the first end 620.

In step 636, after the plunger 606 coupled to the plug 532 has pushed the proximal portion 536 of the plug 532 adjacent to the inner portion 534 of the first opening 524, the plunger 606 is rotated within the cannula 604, causing the plug 532 to couple (also referred to as attach or fasten) with the first opening 524, thereby sealing the first opening 524. In one embodiment, both the proximal portion 536 of the plug 532 and the inner portion 534 of the first opening 524 are threaded, and the rotation of the cannula 604 causes the proximal portion 536 to thread with the inner portion 534, thereby sealing the first opening 524 against expulsion (also referred to as leakage) of the material agent 619 of the load bearing member 514 through the first opening 524.

In step 638, if the first end 620 of the plunger 606 is removably-coupled to the distal end 542 of the plug 532, then after the plug 532 is threaded into the first opening 524 in step 636, the first end 620 of the plunger 606 is decoupled from the distal end 542 and the plunger 606 may be removed from the cannula 604. If the first end 620 of the plunger 606 is breakably-coupled to the distal end 542 of the plug 532 at the joint 626, then after the plug 532 is threaded into the first opening 524 in step 636, further rotation of the plunger 606 causes the first end 620 to break with the distal end 542 of the plug 532 along the joint 626. The plunger 606 may then be removed from the cannula 604.

In step 640, the cannula 604 is rotated within the inserter 602 in the opposite direction as in step 630, thereby de-coupling the cannula 602 from the orthopaedic implant 500. For example, rotating the cannula 604 in the opposite direction unthreads the threaded attachment end 616 of the cannula 604 from the threaded outer portion 530 of the first opening 524, thereby allowing the cannula 604 to be slid out of the tubular portion 608 of the inserter 602.

In step 642, the inserter 602 is de-coupled from the orthopaedic implant 500. In one embodiment, the one or more pins 614 of the attachment portion 610 of the inserter 602 is de-coupled from the one or more second openings 528 of the orthopaedic implant 500.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of charging an orthopaedic implant with a material agent, said orthopaedic implant including an implant body having a first surface, a second surface opposite said first surface, a cavity formed therein that extends through said first surface and said second surface, said implant body being substantially non-porous, said implant body further including a third surface with at least one first opening formed therethrough to said cavity and at least one second opening, said at least one first opening comprising an threaded outer portion having an outer diameter and an threaded inner portion having an inner diameter, said outer diameter greater than said inner diameter, and a load bearing member comprising a substantially porous material held within said cavity, said load bearing member configured to receive, via said at least one first opening, said material agent, said load bearing member having a first contact surface extending out of said cavity past said first surface, said method comprising:
    coupling a tubular assembly to said third surface of said implant body, wherein said tubular assembly includes a tubular passage having a first end and a second end, and wherein said first end is coupled to said third surface such that said tubular passage is centered on said at least one first opening;
    placing said material agent into said tubular passage via said second end;
    sliding a plunger coupled to a plug through said tubular passage via said second end, thereby expelling said material agent from said tubular passage into said load bearing member via said at least one first opening; and
    rotating said plunger within said tubular passage for coupling said plug with said at least one first opening for sealing said at least one first opening against expulsion of said material agent from said load bearing member via said first opening.

2. The method of charging an orthopaedic implant according to claim 1, wherein said tubular assembly comprises an inserter and a cannula, wherein said inserter includes a tubular portion and an attachment portion having at least one pin, wherein said cannula includes a threaded attachment portion, and wherein coupling said tubular assembly to said third surface of said implant body further comprises:
    coupling said at least one pin of said inserter to said at least one second opening of said third surface of said implant body;
    sliding said cannula into said tubular portion of said inserter; and
    coupling said threaded attachment portion of said cannula to said threaded outer portion of said at least one first opening of said third surface,
    wherein said cannula includes said tubular passage.

3. The method of charging an orthopaedic implant according to claim 2, further comprising:
    decoupling said plug from said plunger;
    withdrawing said plunger from said tubular passage via said second end;
    decoupling said cannula from said threaded outer portion of said at least one first opening of said third surface;
    withdrawing said cannula from said tubular portion of said inserter; and
    decoupling said inserter from said at least one second opening of said third surface of said implant body.

4. The method of charging an orthopaedic implant according to claim 3, wherein if said plunger is coupled to said plug via a breakable joint, said decoupling said plug from said plunger comprises rotating said plunger within said tubular passage until said breakable joint breaks.

5. The method of charging an orthopaedic implant according to claim 1, wherein said material agent is a flowable material.

6. The method of charging an orthopaedic implant according to claim 5, wherein said flowable material is a bone graft.

7. The method of charging an orthopaedic implant according to claim 5, wherein said flowable material is a bone putty.

8. The method of charging an orthopaedic implant according to claim 5, wherein said flowable material is a therapeutic.

\* \* \* \* \*

UNITED STATES PATENT AND TRADEMARK OFFICE
CERTIFICATE OF CORRECTION

PATENT NO. : 11,426,291 B2
APPLICATION NO. : 17/076369
DATED : August 30, 2022
INVENTOR(S) : Paul S. Nebosky et al.

It is certified that error appears in the above-identified patent and that said Letters Patent is hereby corrected as shown below:

In the Specification

Column 21
At Line 46, please delete "diameter da", and substitute therefore --diameter $d_d$--.

Signed and Sealed this
Thirtieth Day of July, 2024

Katherine Kelly Vidal
*Director of the United States Patent and Trademark Office*